(12) United States Patent
Ishida et al.

(10) Patent No.: US 8,568,470 B2
(45) Date of Patent: Oct. 29, 2013

(54) GUIDE WIRE AND STENT

(75) Inventors: Kiyohito Ishida, Sendai (JP); Kiyoshi Yamauchi, Sendai (JP); Ryosuke Kainuma, Natori (JP); Yuji Sutou, Sendai (JP); Toshihiro Omori, Sendai (JP); Yuuki Tanaka, Sendai (JP); Hiraku Murayama, Fujinomiya (JP); Ryouichi Souba, Fujinomiya (JP)

(73) Assignees: Japan Science and Technology Agency, Kawaguchi-Shi, Saitama (JP); Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 13/243,651

(22) Filed: Sep. 23, 2011

(65) Prior Publication Data
US 2012/0016463 A1 Jan. 19, 2012

Related U.S. Application Data

(62) Division of application No. 12/108,882, filed on Apr. 24, 2008, now Pat. No. 8,052,620.

(30) Foreign Application Priority Data

May 9, 2007 (JP) .................................. 2007-124871

(51) Int. Cl.
*A61F 2/82* (2013.01)

(52) U.S. Cl.
USPC .......... 623/1.15; 623/1.18; 623/1.19; 623/1.2

(58) Field of Classification Search
CPC ................ A61F 2/82; A61F 2/90; A61F 2/91
USPC .......................................... 623/1.15, 1.18, 19
See application file for complete search history.

(56) References Cited

U.S. PATENT DOCUMENTS

| 4,925,445 A | 5/1990 | Sakamoto et al. |
| 5,069,226 A | 12/1991 | Yamauchi et al. |
| 5,171,383 A | 12/1992 | Sagaye et al. |

(Continued)

FOREIGN PATENT DOCUMENTS

| JP | 1-124473 A | 5/1989 |
| JP | 3-257141 A | 11/1991 |

(Continued)

OTHER PUBLICATIONS

International Search Report dated May 20, 2008 with English language translation of cataegory of cited documents.

(Continued)

*Primary Examiner* — Jason-Dennis Stewart
(74) *Attorney, Agent, or Firm* — Buchanan, Ingersoll & Rooney PC

(57) ABSTRACT

A guide wire includes a distal core member made of a ferrous alloy which has shape memory properties and superelasticity. The ferrous alloy preferably includes substantially two phases, and has a difference of 100° C. or less between an Af point and an Ms point in a thermal hysteresis of martensitic transformation and reverse transformation. The guide wire may include a proximal core member made of an iron-containing alloy and having a higher modulus of elasticity than the distal core member. The two core members may be joined together by welding to form a core of the guide wire.

19 Claims, 15 Drawing Sheets

(56) References Cited

U.S. PATENT DOCUMENTS

| | | | |
|---|---|---|---|
| 5,238,004 | A | 8/1993 | Sahatjian et al. |
| 5,269,759 | A | 12/1993 | Hernandez et al. |
| 5,354,623 | A | 10/1994 | Hall |
| 5,368,049 | A | 11/1994 | Raman et al. |
| 5,402,799 | A | 4/1995 | Colon et al. |
| 5,411,476 | A | 5/1995 | Abrams et al. |
| 5,452,726 | A | 9/1995 | Burmeister et al. |
| 5,497,786 | A | 3/1996 | Urick |
| 5,498,250 | A | 3/1996 | Prather |
| 5,695,111 | A | 12/1997 | Nanis et al. |
| 5,772,609 | A | 6/1998 | Nguyen et al. |
| 5,797,857 | A | 8/1998 | Obitsu |
| 5,876,356 | A | 3/1999 | Viera et al. |
| 5,924,998 | A | 7/1999 | Cornelius et al. |
| 5,951,494 | A | 9/1999 | Wang et al. |
| 6,001,068 | A | 12/1999 | Uchino et al. |
| 6,093,157 | A | 7/2000 | Chandrasekaran |
| 6,165,292 | A | 12/2000 | Abrams |
| 6,234,981 | B1 | 5/2001 | Howland |
| 6,390,992 | B1 | 5/2002 | Morris et al. |
| 6,406,566 | B1 | 6/2002 | Ishida et al. |
| 6,520,923 | B1 | 2/2003 | Jalisi |
| 6,592,570 | B2 | 7/2003 | Abrams et al. |
| 6,602,208 | B2 | 8/2003 | Jafari |
| 6,679,853 | B1 | 1/2004 | Jalisi |
| 6,702,762 | B2 | 3/2004 | Jafari et al. |
| 6,946,040 | B2 | 9/2005 | Homma |
| 7,153,277 | B2 | 12/2006 | Skujins et al. |
| 7,717,864 | B1 | 5/2010 | Grandfield et al. |
| 2003/0069521 | A1 | 4/2003 | Reynolds et al. |
| 2004/0030266 | A1 | 2/2004 | Murayama et al. |
| 2004/0039308 | A1 | 2/2004 | Murayama et al. |
| 2004/0039309 | A1 | 2/2004 | Murayama et al. |
| 2005/0149170 | A1* | 7/2005 | Tassel et al. ................. 623/1.15 |
| 2005/0152731 | A1 | 7/2005 | Mishima et al. |
| 2005/0165441 | A1 | 7/2005 | McGuckin, Jr. et al. |
| 2006/0030933 | A1* | 2/2006 | DeLegge et al. ............. 623/1.19 |
| 2006/0130934 | A1 | 6/2006 | Kuroda et al. |
| 2006/0178727 | A1* | 8/2006 | Richter ........................ 623/1.22 |
| 2006/0200229 | A1* | 9/2006 | Burgermeister et al. ..... 623/1.16 |
| 2006/0235336 | A1 | 10/2006 | Tano et al. |
| 2006/0253187 | A1 | 11/2006 | Moriuchi et al. |
| 2007/0239259 | A1* | 10/2007 | Boylan ........................ 623/1.15 |
| 2008/0091267 | A1* | 4/2008 | Stinson et al. .............. 623/11.11 |

FOREIGN PATENT DOCUMENTS

| | | |
|---|---|---|
| JP | 3-264073 A | 11/1991 |
| JP | 6-063151 A | 3/1994 |
| JP | 9-176729 A | 7/1997 |
| JP | 2000-017395 A | 1/2000 |
| JP | 2003-159333 A | 6/2003 |
| JP | 2003-268501 A | 9/2003 |
| JP | 2004-167045 A | 6/2004 |
| JP | 2004-238720 A | 8/2004 |
| JP | 2006-055245 A | 3/2006 |
| WO | WO 00/50100 A1 | 8/2000 |
| WO | WO 2007/055155 A1 | 5/2007 |

OTHER PUBLICATIONS

English language translation of International Preliminary Report on Patentability issued Nov. 24, 2009 by The International Bureau of WIPO in International Application No. PCT/JP2008/057525.

Hiroyuki Kato et al., "Stress-Induced FCC/FCT Phase Transformation in Fe—Pd Alloy", Scripta Materialia, vol. 46, 2002, pp. 471-475, Pergamon, Acta Materialia Inc., Published by Elsevier Science Ltd.

"Shape-Memory-Alloy and Applications Thereof", Electronic Materials, vol. 41, No. 4, 2002, pp. 56-61.

Official Action (Notification of Reasons for Refusal) issued by Japanese Patent Office on Feb. 19, 2013 in Japanese Application No. 2009-514049 and partial translation (5 pgs).

* cited by examiner

GUIDE WIRE AND STENT

CROSS REFERENCE TO RELATED

This application is a division of pending application Ser. No. 12/108,882 filed Apr. 24, 2008, the contents of which are incorporated herein by reference, which claims priority under 35 U.S.C. §119 to Japanese Application No. 2007-124871 filed May 9, 2007, the entire contents of which are hereby incorporated by reference.

BACKGROUND

The present invention relates to a medical device. More particularly, the invention relates to a guide wire and stent for insertion into a body lumen such as a blood vessel or a bile duct.

One technique that is used in the diagnosis and treatment of conditions such as heart disease involves inserting a guide wire to a target site, then inserting and passing a catheter or the like along the guide wire.

For example, in percutaneous coronary intervention (PCI), first a guide wire is advanced to, then made to traverse, the area of stenosis that is the target site while selecting the branches of the coronary artery under fluoroscopic guidance. Next, a dilatation catheter fitted at the distal end with a balloon is introduced into the body along the guide wire, and the balloon on the catheter is positioned at the stenosis. By then expanding the balloon and enlarging the lumen at the stenosis, blood flow is ensured. Conditions such as angina pectoris can be treated in this way.

Treatment can also be carried out by introducing a self-expanding stent to the target stenosis, and allowing the stent to self-expand at the stenosis.

Titanium-nickel alloys are sometimes used as the material making up such guide wires and stents. When a titanium-nickel alloy is used as the guide wire core, because the pushability and torque transmission of such alloys are inferior to those of materials such as stainless steel, the surface is sometimes coated with a resin to ensure good slideability.

To enhance the torque transmission and other properties, JP 3-264073 A discloses a catheter guide wire core that is a linear body made of a ferrous superelastic metal material, the core being distally tapered so as to become increasingly flexible toward the distal end. Examples of ferrous superelastic metal materials include Fe—Pt, Fe—Pd, Fe—Ni—Co—Ti, Fe—Ni—C, Fe—Mn—Si, Fe—Cr—Mn, Fe—Cr—Mn—Si, Fe—Cr—Ni—Mn—Si and Fe—Cr—Ni—Mn—Si—Co alloys. These are noted as being desirable because they have a high elasticity and are not readily prone to plastic deformation.

In connection with such ferrous superelastic metal materials, JP 03-257141 A, JP 2003-268501 A, JP 2000-17395 A, JP 09-176729 A, and *Scripta Materialia* 46, 471-475 describe Fe—Ni—Co—Al—C alloys, Fe—Ni—Al alloys, Fe—Ni—Si alloys, Fe—Mn—Si alloys and Fe—Pd alloys.

Good superelasticity is not achieved in conventional ferrous alloys because of, at the time of deformation, (a) the introduction of permanent strain such as dislocations, and (b) the formation of irreversible stress-induced lenticular martensite which does not exhibit shape memory effects. To avoid problems (a) and (b), it is effective to improve the strength of the matrix phase in ferrous shape-memory alloys; materials which are precipitation strengthened with an intermetallic compound are particularly effective. It is considerations such as these that have led to the disclosure of the foregoing ferrous alloys.

Although Ti—Ni alloys such as the above are sometimes used in guide wires and stents, the superelastic strain region for Ti—Ni alloys is at best about 8%; when a larger deformation is applied, the alloy undergoes plastic deformation, which is undesirable. It would be preferable to use a material having a broader superelastic strain region than Ti—Ni alloys as the guide wire and stent material.

In cases where a Ti—Ni alloy is used as the core material on the distal portion of a guide wire, a ferrous alloy is used as the core material on the proximal portion, and these core materials are welded together to form a single guide wire core, the fact that the Ti—Ni alloy is a different material which has, in particular, a poor weldability with ferrous alloys, imposes limitations on the materials to which it can be bonded and the bonding conditions. In medical devices for insertion and extended placement within the body in particular, the device must be manufactured while taking the greatest possible care to avoid the possibility of the weld failing within the body; hence the need for special bonding conditions, etc.

As noted above, in some cases where a Ti—Ni alloy is used as the guide wire core, the surface is coated with a resin. However, when a plastic material having a high melting point, such as a fluorocarbon resin, is used as the resin, the properties of the Ti—Ni alloy may change under the influence of the high temperature. The distal portion of the guide wire core, while slender, undergoes repeated bending and twisting. To be able to withstand such use, the resin coated onto the surface must have an improved peel resistance.

In addition, stents made of Ti—Ni alloys are sometimes of insufficient strength and durability. It is especially difficult to satisfy the requirements for strength and durability in stents used at placement sites where there is a lot of movement, such as the legs. Also, while it is preferable for a stent to be thin-walled, the strength in such cases decreases even further. Hence, thin-walled Ti—Ni alloy stents are often unable to withstand normal use.

Guide wires and stents made of Ti—Ni alloys also lack a good visibility under fluoroscopic imaging. To enable the insertion site and placement site to be verified under fluoroscopic imaging, a high-contrast member made of gold or the like must be bonded to the distal end of the guide wire and the ends of the stent.

The ferrous metal materials listed in JP 3-264073 A as preferable for use in guide wires are referred to as being "superelastic," yet the amount of strain from which superelastic recovery is possible in such materials is in fact less than 1%, which hardly satisfies the properties required of a guide wire core.

Nor do JP 03-257141 A, JP 2003-268501 A and JP 2000-17395 A make any mention of such properties of practical importance as the amount of strain from which superelastic recovery is possible, the percent recovery, and the superelastic operating temperature ranges for Fe—Ni—Co—Al—C alloys, Fe—Ni—Al alloys and Fe—Ni—Si alloys.

*Scripta Materialia* 46, 471-475 reports on the superelasticity of Fe—Pd alloys containing unusually large amounts of costly palladium, but such alloys have an amount of strain from which superelastic recovery is possible of less than 1%, which is small, and thus cannot be regarded as having a good superelasticity. Moreover, these alloys are difficult to produce.

JP 09-176729 A mentions that Fe—Mn—Si alloys are nonmagnetic but, by utilizing a fcc/hcp transformation, exhibit a shape memory effect and superelasticity. However, there are limitations on the temperatures at which such Fe—Mn—Si alloys can be used because the superelasticity is achieved at temperatures higher than room temperature.

Moreover, these alloys have a poor corrosion resistance and cold workability, complicated thermomechanical treatment is required to achieve further superelasticity, and there are problems with the manufacturability.

SUMMARY

A guide wire includes a member having a ferrous alloy. According to one aspect, the ferrous alloy may have shape memory properties and superelasticity, include substantially two phases having a γ phase and a γ' phase, and have a difference of 100° C. or less between a reverse transformation finish temperature and a martensitic transformation start temperature in a thermal hysteresis of martensitic transformation and reverse transformation. The guide wire also includes a proximal core member which is made of an iron-containing alloy and has a higher modulus of elasticity than the distal core member. The distal core member and the proximal core member are joined together by welding to form a core of the guide wire. The proximal core member preferably is made of stainless steel or is piano wire. The guide wire may include a tubular member which covers the distal core member. The tubular member preferably is a coil. The tubular member preferably is made of plastic.

According to another aspect, a guide wire may includes a proximal tube which may be made of a metallic material having a higher modulus of elasticity than the ferrous alloy and which covers at least part of the proximal portion of the core, the ferrous alloy has shape memory properties and superelasticity, includes substantially two phases having a γ phase and a γ' phase, and has a difference of 100° C. or less between a reverse transformation finish temperature and a martensitic transformation start temperature in a thermal hysteresis of martensitic transformation and reverse transformation. The guide wire may preferably further include a tubular member which covers a distal portion. The tubular member may be made of plastic.

According to further aspect, a guide wire may include a coating which has at least one layer and covers at least part of a surface of the proximal core member, the at least one layer of the coating is made of a fluorocarbon resin, and the ferrous alloy has shape memory properties and superelasticity, includes substantially two phases having a γ phase and a γ' phase, and has a difference of 100° C. or less between a reverse transformation finish temperature and a martensitic transformation start temperature in a thermal hysteresis of martensitic transformation and reverse transformation.

A stent includes a body made of a ferrous alloy. According to another aspect, the ferrous alloy preferably has shape memory properties and superelasticity, includes substantially two phases having a γ phase and a γ' phase, and has a difference of 100° C. or less between a reverse transformation finish temperature and a martensitic transformation start temperature in a thermal hysteresis of martensitic transformation and reverse transformation. The body preferably has a plurality of undulating bends provided in an axial direction. The body is preferably composed of braided wire.

According to furthermore aspect, a medical device includes a first member including a ferrous alloy. A second member may be joined with the first member. A member, for example a wire, a plate, a pipe or a rod, is made of a ferrous alloy having shape memory properties and superelasticity, including substantially two phases having a γ phase and a γ' phase, and having a difference of 100° C. or less between a reverse transformation finish temperature and a martensitic transformation start temperature in a thermal hysteresis of martensitic transformation and reverse transformation, the ferrous alloy including a composition which includes from 25 to 35% by mass of nickel, from 10 to 30% by mass of cobalt, and from 2 to 8% by mass of aluminum, the composition including a total of from 1 to 20% by mass of at least one selected from the group consisting of from 1 to 5% by mass of titanium, from 2 to 10% by mass of niobium, from 3 to 20% by mass of tantalum, and the balance being from 35 to 50% by mass of iron and inadvertent impurities. An abundance of a specific crystal orientation in a working direction for the ferrous alloy preferably is at least 2.0. The medical device may be a guide wire.

The guide wire of an embodiment according to a first aspect (also referred to below as "guide wire (A)") includes a core having a distal core member made of a ferrous alloy (also referred to below as "the ferrous alloy of the invention") which has shape memory properties and superelasticity, consists substantially of two phases having a γ phase and a γ' phase, and has a difference of 100° C. or less between a reverse transformation finish temperature and a martensitic transformation start temperature in a thermal hysteresis of martensitic transformation and reverse transformation, and a proximal core member which is made of an iron-containing alloy and has a higher modulus of elasticity than the distal core member, the distal core member and proximal core member being joined together by welding. The guide wire has a broad superelasticity region and a high Young's modulus, and is thus endowed with both suppleness and pushability. Moreover, the guide wire has an excellent weldability between the distal core member and the proximal core member. In addition, when coated on the surface with a high-melting plastic material such as a fluorocarbon resin, this guide wire is not readily affected by heat treatment and has an excellent slideability. This guide wire also has an excellent fluoroscopic visibility. Furthermore, it uses a superelastic ferrous alloy that is relatively easy to produce. In addition, this guide wire has a smaller LPS (recovery stress)—a tensile property—than Ti—Ni alloys, and is thus more gentle on blood vessels. Finally, because the maximum tensile strength is higher than that of Ti—Ni alloys, this guide wire has a high safety even after it has been tapered.

The guide wire of an embodiment according to a second aspect (also referred to below as "guide wire (B)") includes a core having distal and proximal portions, of which at least the distal portion is made of the ferrous alloy of the invention, and a proximal tube which is made of a metallic material having a higher modulus of elasticity than the ferrous alloy making up the core and which covers at least part of the proximal portion of the core. This guide wire (B), owing to a broad superelasticity region and a high Young's modulus, is endowed with both suppleness and pushability. Moreover, when coated on the surface with a high-melting plastic material such as a fluorocarbon resin, it is not readily affected by heat treatment and has an excellent slideability. In addition, this guide wire has an excellent bondability between the distal core and the proximal tube. This guide wire also has an excellent fluoroscopic visibility. Furthermore, it is made using a superelastic ferrous alloy that is relatively easy to produce.

The guide wire of an embodiment according to a third aspect (also referred to below as "guide wire (C)") includes a distal core member and a proximal core member, each made of a ferrous alloy, and a coating which is composed of at least one layer and covers at least part of a surface of the proximal core member, at least one layer of the coating being made of a fluorocarbon resin. This guide wire (C), owing to a broad superelasticity region and a high Young's modulus, is endowed with both suppleness and pushability. Moreover, it is a guide wire which, when coated on the surface with a high-melting plastic material such as a fluorocarbon resin, is not readily affected by heat treatment and has an excellent slideability. In addition, it has an excellent fluoroscopic visibility.

The stent of an embodiment according to a fourth aspect, which includes a body composed of a ferrous alloy, is endowed with excellent strength and durability. The stent has excellent fluoroscopic visibility. Moreover, the body is composed of a superelastic ferrous alloy that is relatively easy to produce.

The invention can provide such guide wires and stents.

BRIEF DESCRIPTION OF THE DIAGRAMS

In the accompanying drawings:

FIG. 1 is a longitudinal sectional view showing a first embodiment of a guide wire (A) according to one aspect of the present invention;

FIG. 2 presents diagrams illustrating a procedure for connecting together the distal core member and the proximal core member in the guide wire (A) shown in FIG. 1;

DETAILED DESCRIPTION

First, the guide wire (A) of a first embodiment according to one aspect of the invention is described in detail based on the preferred embodiments shown in the attached diagrams.

Figure 1:
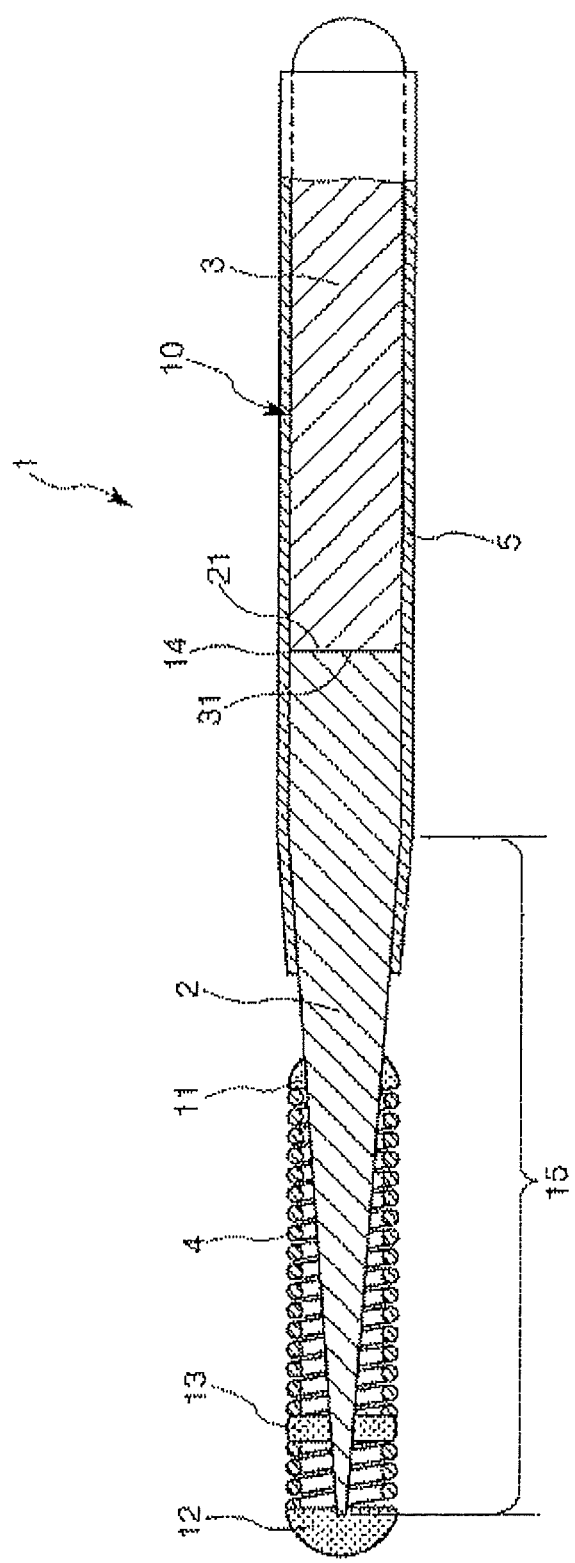
Figure 2:
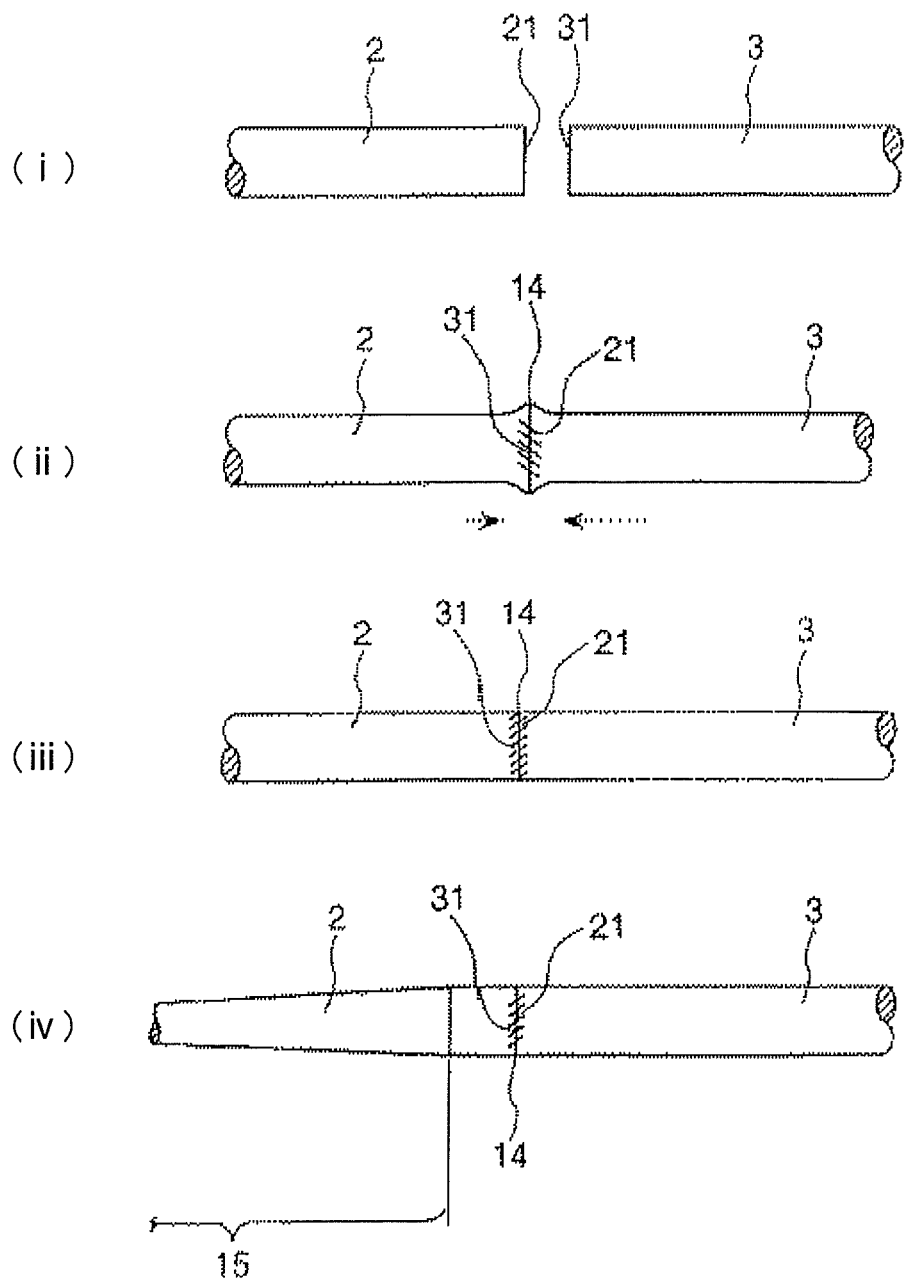
Figure 3:
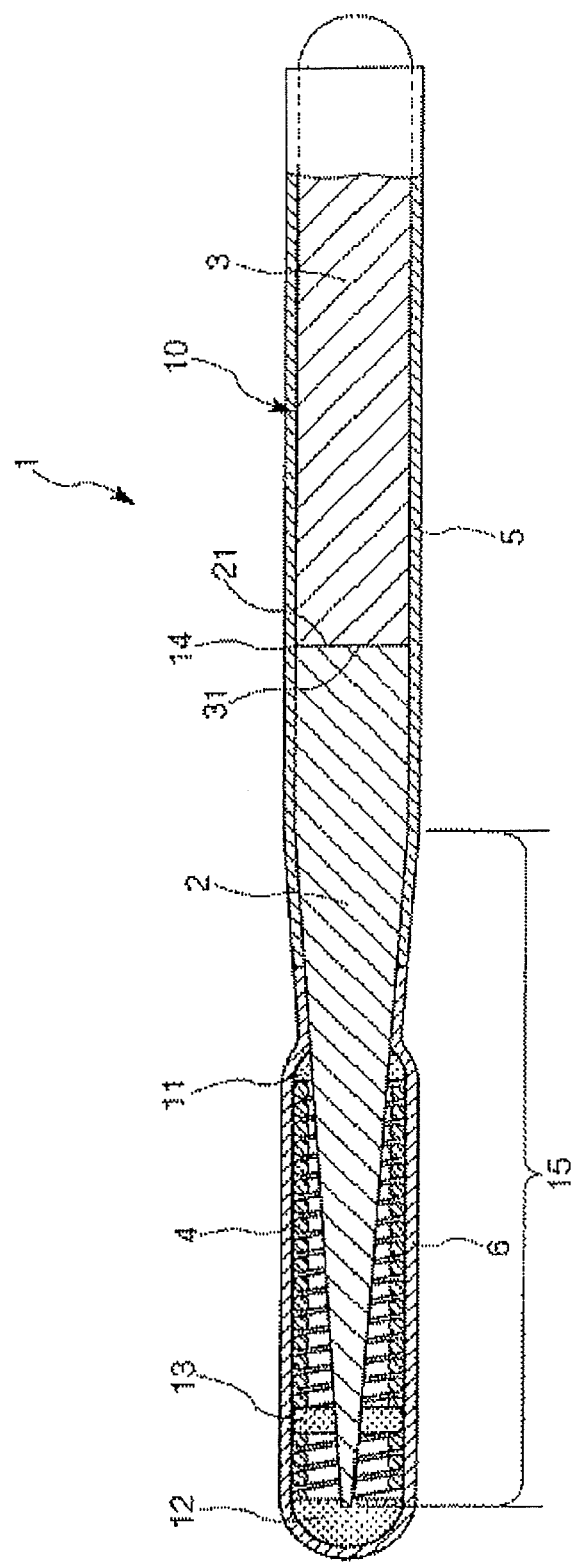
FIG. 3 is a longitudinal sectional view showing a second embodiment of a guide wire (A)

FIG. 1 is a longitudinal sectional view showing a first embodiment of a guide wire (A) according to one aspect of the invention; FIG. 2 presents diagrams illustrating a procedure for connecting together the distal core member and the proximal core member in the guide wire (A) shown in FIG. 1; and FIG. 3 is a longitudinal sectional view showing a second embodiment of a guide wire (A) according to the aspect of the invention. For the sake of convenience, in FIGS. 1 and 2, the portion of the guide wire appearing on the right side of the diagram is referred to herein as the "proximal side" and the portion of the guide wire appearing on the left side of the diagram is referred to as the "distal side." Moreover, in FIGS. 1 and 2, the guide wire is shown schematically so as to appear shortened in the length direction and exaggerated in the thickness direction, as a result of which the ratio between the length direction and the thickness direction as shown in the diagrams differs considerably from the actual ratio (the same applies also to the subsequently described diagram in FIG. 3).

A guide wire 1 shown in FIG. 1 is a catheter guide wire for use by insertion into a catheter. The guide wire 1 has a core 10 obtained by welding and thereby joining together a distal core member 2 disposed on the distal side and a proximal core member 3 disposed on the proximal side of the distal core member 2, and also has a helical coil 4. The guide wire 1 has a total length which, while not subject to any particular limitation, is preferably in a range of from about 200 mm to about 5,000 mm. The core 10 has an outer diameter (referring to the outer diameter of that portion of the core 10 where the outer diameter is constant) which, while not subject to any particular limitation, is preferably in a range of from about 0.2 mm to about 1.2 mm.

The distal core member 2 is a wire having elasticity which is composed of the ferrous alloy of the invention. The distal core member 2 has a length which, while not subject to any particular limitation, is preferably in a range of from about 20 mm to about 1,000 mm.

In the present embodiment, the distal core member 2 has a constant diameter over a given length from the proximal end thereof, then gradually tapers toward the distal direction starting at some intermediate point. This latter portion is referred to herein as the tapering diameter portion 15. By having such a tapering diameter portion 15, the rigidity (flexural rigidity, torsional rigidity) of the distal core member 2 can be gradually reduced in the distal direction. As a result, the guide wire 1 achieves a good flexibility in the distal portion, thus improving the safety and the ability of the guide wire 1 to navigate a blood vessel, and preventing undesirable effects such as kinking.

In the illustrated arrangement, the tapering diameter portion 15 is formed over part of the distal core member 2, although it is also possible for the tapering diameter portion 15 to make up the entire distal core member 2. The angle of taper (rate of reduction in the outer diameter) on the tapering diameter portion 15 may be constant along the length of the wire or there may be points along the length where the angle of taper changes. For example, a plurality of places where the angle of taper is relatively large and a plurality of places where the angle of taper is relatively small may be repeatedly formed in alternation.

Or the distal core member 2 may have a portion with an outer diameter that is constant in the lengthwise direction, either partway along the tapering diameter portion 15 or distal to the tapering diameter portion 15. For example, the distal core member 2 may have formed, at a plurality of places in the lengthwise direction, tapered portions on which the outer diameter tapers in the distal direction, and may have formed, between one such tapered portion and another such tapered portion, a portion having a constant outer diameter in the lengthwise direction. The effects achieved in such cases are the same as those indicated above.

Alternatively, unlike the arrangement shown in the foregoing diagrams, it is possible for the guide wire 1 to have a configuration in which the proximal end of the tapering diameter portion 15 is situated partway along the proximal core member 3; i.e., the tapering diameter portion 15 is formed so as to straddle the interface (weld 14) between the distal core member 2 and the proximal core member 3.

The material making up the distal core member 2 is the ferrous alloy of the invention, which is described more fully later in the specification.

Compared with stainless steel, the ferrous alloy of the invention is flexible, in addition to which it has resilience and is not readily subject to deforming plastically. Therefore, by having the distal core member 2 made of the ferrous alloy of the invention, the guide wire 1 is able to achieve in the distal portion thereof both sufficient flexibility and sufficient resilience to bending, enhancing the ability of the guide wire to navigate highly tortuous vasculature, and thus providing an even better operability. Moreover, even when the distal core member 2 is repeatedly curved and bent, because of its resilience, the distal core member 2 does not deform plastically, making it possible to prevent a decline in operability during use of the guide wire 1 due to plastical deforming of the distal core member 2. Furthermore, because the ferrous alloy of the invention has a higher Young's modulus than Ti—Ni alloys, the distal core member 2 retains a suppleness even when the diameter is reduced, and thus exhibits the above-described operability.

The distal end of the proximal core member 3 is joined to the proximal end of the distal core member 2 by welding. The proximal core member 3 is in the form of a wire having elasticity. The length of the proximal core member 3, while not subject to any particular limitation, is preferably from about 20 mm to about 4,800 mm.

The proximal core member 3 is made of a material having larger moduli of elasticity (Young's modulus (longitudinal elastic modulus), modulus of rigidity (modulus of transverse elasticity), volumetric elastic modulus) than the material making up the distal core member 2. In this way, a suitable rigidity (flexural rigidity, torsional rigidity) can be achieved in the proximal core member 3, giving the guide wire 1 a good stiffness that enhances pushability and torque transmission, enabling a better operability to be achieved during insertion of the guide wire 1.

The material making up the proximal core member 3 is not subject to any particular limitation, provided it is an iron-containing alloy (either iron or steel). Preferred examples of materials that may be used include stainless steels (any SUS grade, such as SUS 304, SUS 303, SUS 316, SUS 316L, SUS 316J1, SUS 316J1L, SUS 405, SUS 430, SUS 434, SUS 444, SUS 429, SUS 430F and SUS 302) and piano wire.

When a stainless steel is used as the material making up the proximal core member 3, the guide wire (A) of the invention is able to achieve an even better pushability and torque transmission.

Piano wire is desirable because it has a high modulus of elasticity and a suitable elastic limit.

In the arrangement shown in the diagram, the proximal core member 3 has a substantially constant outer diameter over substantially its entire length. However, it may have places in the lengthwise direction where the outer diameter changes.

The coil 4 is a member composed of a fine, helically coiled wire, and is disposed so as to cover the distal portion of the distal core member 2. In the illustrated arrangement, the distal portion of the distal core member 2 has been inserted into the coil 4 to substantially the center thereof. Moreover, the distal portion of the distal core member 2 has been inserted therein without being in contact with the inside wall of the coil 4. The weld 14 is situated proximal to the proximal end of the coil 4.

In the illustrated arrangement, the coil 4, which is shown in a state where no outside forces are applied thereto, has small gaps open between adjoining turns of the helically coiled wire. Alternatively, unlike the illustrated arrangement, when the coil is in a state where no outside forces are applied thereto, it is also possible for the helically coiled wire to be tightly arranged without intervening gaps between adjoining turns.

The coil 4 is preferably made of a metallic material. Examples of suitable metallic materials include stainless steels, superelastic alloys, cobalt alloys, precious metals such as gold, platinum and tungsten, and alloys containing such precious metals.

A radiopaque material such as a precious metal may be used for this purpose. However, even if such a radiopaque material is not used, because the ferrous alloy of the invention is fluoroscopically visible, the guide wire 1 which includes the above-described distal core member 2 will have fluoroscopic visibility and will thus be capable of insertion into the body while tracking the position of the distal end under fluoroscopic control. Although the quality of the fluoroscopic visibility is related to the density of the metallic material used, in the case of Ti—Ni alloys, because the titanium which accounts for substantially half of the alloy has a relatively low density of 4.54 g/cm$^3$, slender portions such as the distal core member are sometimes difficult to identify under x-ray fluoroscopy. By contrast, as shown in Table 1, the iron, nickel and cobalt which are the chief ingredients in the ferrous alloys of the invention have respective densities of 7.86 g/cm$^3$, 8.85 g/cm$^3$ and 8.8 g/cm$^3$, which are much higher than the density of titanium. Hence, such ferrous alloys have a higher density overall than Ti—Ni alloys, making even the slender portions of the distal core member easier to track under fluoroscopy.

The coil 4 may be made of a different material than the distal core member 2 and the proximal core member 3 of the guide wire 1. The overall length of the coil 4, while not subject to any particular limitation, is preferably from about 5 mm to about 500 mm.

The proximal and distal ends of the coil 4 are respectively secured to the distal core member 2 by fixing materials 11 and 12. In addition, an intermediate point (located closer to the distal end) of the coil 4 is secured to the distal core member 2 by a fixing material 13. Fixing materials 11, 12 and 13 are made of solder (braze). However, fixing materials 11, 12 and 13 are not limited to solder, and may even be adhesives. Methods for securing the coil 4 are not limited to methods involving the use of a fixing material, and include also, for example, soldering. To prevent the guide wire from damaging the inside wall of the blood vessel, it is preferable for the distal endface of the fixing material 12 to be rounded.

In the present embodiment, because such a coil 4 is provided thereon, the distal core member 2 is covered by the coil 4 and has a small surface area of contact. This enables the sliding resistance to be decreased, which further enhances the operability of the guide wire 1.

In the present embodiment, a wire having a round cross-section is used in the coil 4. However, the wire is not limited to this cross-sectional shape; wires of other cross-sectional shapes, such as elliptical or quadrangular (particularly rectangular) shapes, may instead be used for the same purpose.

In the guide wire 1, the distal core member 2 and the proximal core member 3 are mutually coupled (fixed) by welding. In this way, a high coupling strength (bond strength) can be achieved at the weld (junction) 14 between the distal core member 2 and the proximal core member 3, enabling torsional torque and pushing forces from the proximal core member 3 of the guide wire 1 to be reliably transmitted to the distal core member 2.

It is preferable for the outer periphery of the weld 14 to be rendered substantially smooth by a method such as the subsequently described procedures (iii) and (iv).

In the present embodiment, the distal core member 2 has a connecting endface 21 for connection to the proximal core member 3, and the proximal core member 3 has a connecting endface 31 for connection to the distal core member 2 that are each flat planes substantially perpendicular to the axial direction (lengthwise direction) of both cores. This arrangement greatly facilitates the working operations required to shape the connecting endfaces 21 and 31, enabling the above-described effects to be achieved without further complicating the guide wire 1 manufacturing process.

Alternatively, unlike in the diagrams, the connecting endfaces 21 and 31 may be angled with respect to a plane perpendicular to the axial direction (lengthwise direction) of both core members 2 and 3, or may even be concave or convex.

Examples of methods for welding together the distal core member 2 and the proximal core member 3, while not subject to any particular limitation, include laser welding, and butt resistance welding techniques such as upset welding and flash welding. A butt resistance welding technique is preferred for achieving the weld 14 having a higher bond strength.

Next, referring to FIG. 2, the steps involving in joining together the distal core member 2 and the proximal core member 3 by upset welding, which is one type of butt resistance welding technique, are described. FIG. 2 shows steps (i) to (iv) involved in joining together the distal core member 2 and the proximal core member 3 by upset welding.

Step (i) shows a distal core member 2 and a proximal core member 3 which are secured to (mounted on) a butt welding machine (not shown).

In step (ii), the connecting endface 21 on the proximal end of the distal core member 2 and the connecting endface 31 on the distal end of the proximal core member 3 are brought into pressurized contact by the butt welding machine while a predetermined voltage is applied. Under this pressurized contact, a molten layer forms at the areas in contact, thereby securely connecting the distal core member 2 with the proximal core member 3.

In step (iii), a protruding area that has arisen at the place of connection (weld 14) due to deformation by the pressurized contact is removed, thereby making the outer periphery of the weld 14 substantially smooth. Methods for removing such a protruding area include grinding, polishing, and chemical treatment such as etching.

Next, in step (iv), areas of the distal core member 2 which are distal to the place of connection (weld 14) are ground or polished so as to form a tapering diameter portion 15 in which the outer diameter gradually decreases toward the distal end.

In cases where the proximal end of the tapering diameter portion 15 is proximal to the weld 14, step (iv) may be carried out without first carrying out step (iii).

In the guide wire (A) of the embodiment, the proximal core member is made of a SUS grade or other type of stainless steel. After the distal core member and the proximal core member have been welded together, it is advantageous to subject the proximal end of the distal core member to hardening treatment.

Because the distal core member is more flexible than the proximal core member, when the outer diameters of both core members are about the same, the difference between the rigidities of the two core members on either side of the weld is large. However, it appears that the difference in rigidities can be reduced by subjecting the proximal end of the distal core member to hardening treatment.

The fact that the distal core member made of the ferrous alloy of the invention has a broader superelasticity region than Ti—Ni alloys, taken together with the difference in rigidities, means that bending occurs at the distal side of the weld, leading to stress concentration at the weld. However, it is believed that by carrying out hardening treatment as described above and thus reducing the difference between the rigidities of the two core members, stress concentration at the weld will be suppressed so that even when strongly flexed, the guide wire will curve smoothly without localized bending.

Examples of hardening treatment include aging and peening. When hardening is carried out by aging, hardening occurs by the precipitation of intermetallic compounds such as $Ni_3Al$ on the proximal side of the distal core member. The amount of precipitate on the proximal side of the distal core member is higher than in untreated areas. In peening, the surface layer can be work-hardened, enhancing the rigidity. In both of these hardening treatments, it is preferable to carry out treatment so that the flexibility gradually increases toward the distal end. Also, it is desirable to reduce the diameter at the distal end of the proximal core member so as to make it more flexible than other portions of the proximal core member and thereby reduce the difference in rigidity.

In the guide wire 1 shown in FIG. 1, the core 10 has a coating 5 which covers all or part of the outer peripheral surface (outside surface) of the guide wire 1. This coating 5 may be formed for a number of purposes, one of which is to reduce friction (sliding resistance) by the guide wire 1, thus improving slideability and in turn enhancing the operability of the guide wire 1.

To achieve this purpose, it is preferable for the coating 5 to be made of a material capable of lowering friction. In this way, frictional resistance (sliding resistance) with the inside wall of the catheter used together with the guide wire 1 decreases, improving slideability and resulting in even better operability of the guide wire 1 within the catheter. Also, because the guide wire 1 has a lower sliding resistance, when the guide wire 1 is moved and/or rotated inside the catheter, kinking and twisting of the guide wire 1, especially kinking and twisting in the vicinity of the weld, can be more reliably prevented.

Examples of such materials capable of reducing friction include polyolefins such as polyethylene and polypropylene, polyvinyl chloride, polyesters (e.g., PET, PBT), polyamides, polyimides, polyurethanes, polystyrenes, polycarbonates, silicone resins, fluorocarbon resins (e.g., PTFE, ETFE), and various other elastomers, as well as composite materials thereof.

Of the above, when a fluorocarbon resin (or a composite material containing the same) is used, the frictional resistance (sliding resistance) between the guide wire 1 and the catheter inside wall can be more effectively reduced, enabling the slideability to be improved, and thus making it possible to achieve an even better guide wire 1 operability within the catheter. Moreover, it is possible in this way to more reliably prevent kinking and twisting of the guide wire 1, and especially kinking and twisting in the vicinity of the weld, when the guide wire 1 is moved and/or rotated inside the catheter.

When a fluorocarbon resin (or a composite material containing the same) is used, the resin material is generally coated onto the core 10 in a heated state by a process such as baking or blowing, thereby resulting in an exceptionally good adhesion between the core 10 and the coating 5.

The fluorocarbon resin coated in this way onto the core 10 is generally baked at about 300 to 400° C., although the ferrous alloy of the invention is not readily affected by such temperatures and is thus resistant to changes in its properties.

When the coating 5 is composed of a fluorocarbon resin such as PTFE or PFA, another coating (undercoat) may also be provided between the core 10 and the coating 5. Adhesion between the coating and the undercoat can be improved by having the undercoat be composed of a mixture of a heat-resistance resin such as a polyimide, polyamide or polyamideimide with a fluorocarbon resin such as PTFE or PFA. In this way, the core 10 made of a ferrous alloy having a wide superelasticity region can be provided with an ability to navigate bends and twists in the vasculature and, owing to the coating 5 made of a fluorocarbon resin, can also be endowed with a good slideability.

Other preferred materials capable of reducing friction include hydrophilic materials.

Illustrative examples of such hydrophilic materials include cellulose-based polymeric substances, polyethylene oxide-based polymeric substances, maleic anhydride-based polymeric substances (e.g., maleic anhydride copolymers such as methyl vinyl ether-maleic anhydride copolymers), acrylamide-based polymeric substances (e.g., polyacrylamides, polyglycidyl methacrylate-dimethylacrylamide (PGMA-DMAA) block copolymers), water-soluble nylons, polyvinyl alcohols and polyvinylpyrrolidone.

Such hydrophilic materials often exhibit lubricity on wetting (water absorption), lowering the frictional resistance (sliding resistance) with the inside walls of the catheter used together with the guide wire 1. As a result, the slideability of the guide wire 1 is improved, and the guide wire 1 has an even better operability within the catheter.

The coating 5 is preferably made of a thermoplastic elastomer. Because the distal core member is made of the ferrous alloy of the invention, it can be deformed in a broader superelasticity region than Ti—Ni alloys. However, even when the distal core member made of the inventive ferrous alloy is subjected to large deformation, because the coating is made of a thermoplastic elastomer, stretching by the coating conforms to deformation of the distal core member, as a result of which the coating does not readily peel from the distal core member.

Examples of the thermoplastic elastomer include polyurethane elastomers and polyamide elastomers. It is desirable to coat the outside surface of the coating 5 made of a thermoplastic elastomer with a hydrophilic material.

While such a coating 5 may be formed either over the entire length of the core 10 or over a portion of the core 10 in the lengthwise direction, it is preferable to form the coating in places that include the weld so as to cover the weld 14. In this way, even in the unlikely event that bumps, flash or the like should arise on the outer periphery of the weld 14, such areas are covered by the coating 5, enabling slideability to be ensured. Moreover, the coating 5 has a substantially uniform outer diameter, further enhancing the slideability.

The coating 5 has an average thickness which, while not subject to any particular limitation, is preferably from about 1 µm to about 20 µm, and more preferably from about 2 µm to about 10 µm. If the coating 5 is too thin, the purpose of forming the coating 5 may not be fully achieved, and peeling of the coating 5 may arise. On the other hand, the coating 5 which is too thick may interfere with the properties of the wire and may also lead to peeling of the coating 5.

In the guide wire (A) of the embodiment, treatment (e.g., chemical treatment, heat treatment) may be additionally carried out to improve adhesion of the coating 5 to the outside peripheral surface of the core 10, or to provide an intermediate layer capable of enhancing adhesion of the coating 5.

Next, a second embodiment of the guide wire (A) is described while referring to FIG. 3, with particular reference to those features which differ from the foregoing first embodiment of the invention. Descriptions of like features are omitted.

In the guide wire 1 shown in FIG. 3, a first coating 5 has a distal end located at a position proximal to the proximal end of the coil 4, and a second coating 6 differing from the first coating 5 is formed distal to the first coating 5.

The guide wire (A) may thus have two or more coatings. Moreover, the coatings may partially or completely overlap.

The second coating 6 is provided so as to cover part or all of the coil 4. In the arrangement shown in FIG. 3, the second coating 6 covers the entire coil 4.

The material making up such a second coating 6 may be the same as or different from those mentioned above in connection with the earlier described coating 5. Examples of suitable materials for this purpose include plastics, and more specifically, polyolefins such as polyethylene and polypropylene, polyvinyl chloride, polyesters (e.g., PET, PBT), polyamides, polyimides, polyurethanes, polystyrenes, polycarbonates, fluorocarbon resins, silicone resins, silicone rubbers, and various other elastomers (e.g., polyamide-based and polyester-based thermoplastic elastomers).

As noted above, the materials making up the first coating 5 and the second coating 6 are not subject to any particular limitation. However, it is preferable for the first coating to be made of a silicone resin (or a composite material including the same), and for the second coating 6 to be made of a fluorocarbon resin (or a composite material including the same).

In this way, the coatings can be made to possess both the advantages of silicone resins and the advantages of fluorocarbon resins described above. That is, by combining the first coating 5 material and the second coating 6 material in the above way, the entire guide wire 1 can be endowed with a sufficient slideability and an excellent operability while retaining a good bond strength between the distal core member 2 and the proximal core member 3 at the weld 14.

Alternatively, in cases where the first coating 5 is made of a fluorocarbon resin (or a composite material containing the same) and the second coating 6 is made of a polyurethane resin (or a composite material containing the same), substances having good angiographic properties may be mixed into the polyurethane resin, enabling the visibility under fluoroscopic imaging to be improved. Also, by having the polyurethane coating cover the underlying metal, safety is enhanced because, for example, the risk of intravascular failure by the wire can be avoided. The hydrophilic material coated onto the surface of the second coating 6 improves lubricity. Fluorocarbon resin-covered areas are desirable because they have a good slideability within the catheter.

In cases where the first coating 5 is made of a hydrophobic resin and the second coating 6 is made of a hydrophilic resin, the guide wire 1 has an especially good slideability within the catheter and an excellent threadability through vascular lumens.

The second coating has an average thickness which, while not subject to any particular limitation, is preferably from about 1 µm to about 20 µm, and more preferably from about 2 µm to about 10 µm. The second coating 6 has a thickness which may be the same as or different from that of the first coating 5.

The guide wire (A) of the present embodiment may be one that is not fitted with a coil 4, in which case the above-described second coating 6 may or may not be provided in the same places as indicated above.

That is, the guide wire (A) may be one which lacks a coil 4 and in which a coating composed of a plastic such as one of those mentioned above is provided in place of the coil 4. For example, the guide wire (A) may have a plastic coating which is made of the same material as the above-described first coating 5 or second coating 6, and which is provided as a tubular member for covering the distal portion of the above-described core. It is preferable for the plastic coating to be composed of a polyurethane resin (or a composite material containing the same). The reason is that substances having good angiographic properties may be mixed into the polyurethane resin, enabling the visibility under fluoroscopic guidance to be improved. Moreover, it is also preferable for the plastic coating to be composed of a polyurethane resin and to have a coating 5 made of a fluorocarbon resin. Here too, the reason is that substances having good angiographic properties may be mixed into the polyurethane resin, enabling the visibility under fluoroscopic guidance to be improved. An additional reason is that by having polyurethane cover the metal, doctors can satisfy because, for example, the occurrence of intravascular failure by the wire can be avoided. Also, by coating a hydrophilic material onto the surface of the polyurethane resin, a good lubricity is achieved. The first coating 5 made of a fluorocarbon resin has a good slideability within the catheter.

In the arrangement shown in FIG. 3, the distal end of the first coating 5 and the proximal end of the second coating 6 are bonded together and formed so that the two layers are continuous. Alternatively, the distal end of the first coating 5 and the proximal end of the second coating 6 may be located away from each other, or the first coating 5 and the second coating 6 may partially overlap.

Figure 4:
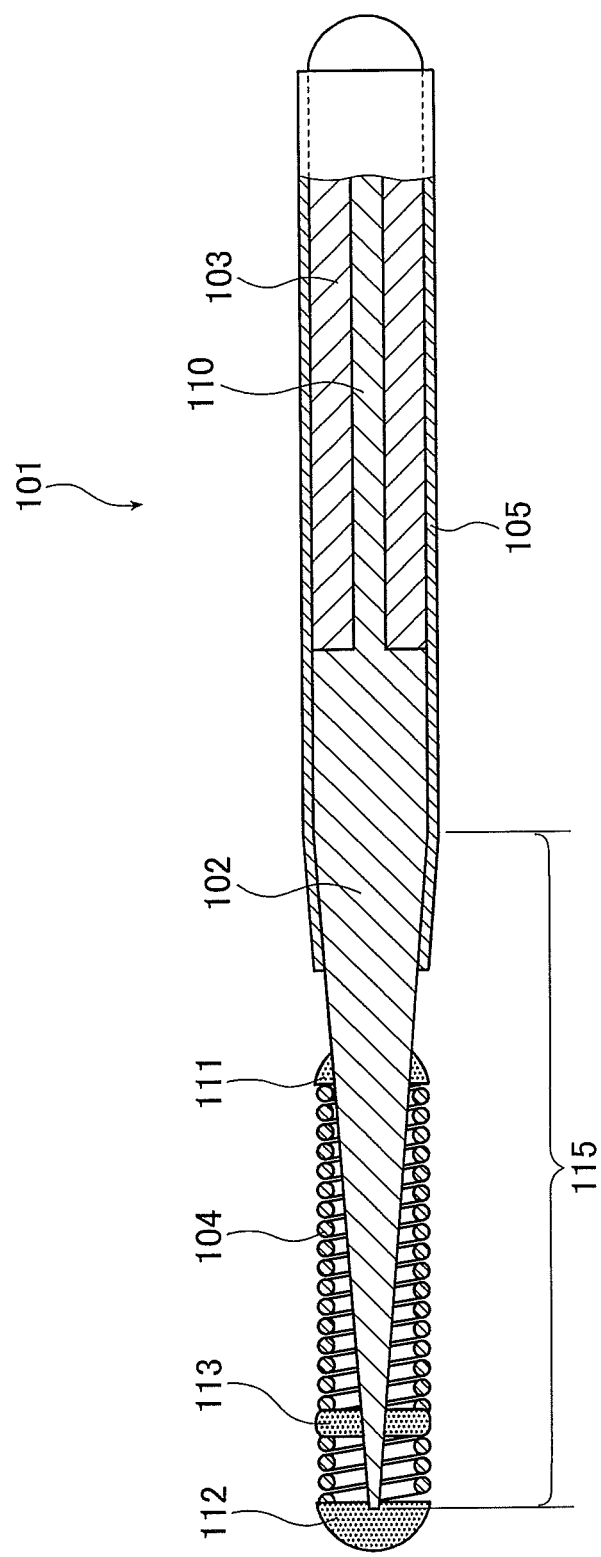
FIG. 4 is a longitudinal sectional view showing a first embodiment of a guide wire (B) according to another aspect of the invention.

Next, a preferred embodiment of another guide wire (B) according to another aspect of the present invention is described in detail while referring to FIG. 4.

FIG. 4 is a longitudinal sectional view of an embodiment of a guide wire (B) according to another aspect of the invention. For the sake of convenience, in FIG. 4 and in subsequently described FIG. 5, the portion of the guide wire appearing the right side of the diagram is referred to herein as the "proximal side" and the portion of the guide wire appearing on the left side of the diagram is referred to as the "distal side." In FIG. 4 and subsequently described FIG. 5, the guide wire is shown schematically so as to appear shortened in the length direction and exaggerated in the thickness direction, as a result of which the ratio between the length direction and the thickness direction as shown in the diagrams differs considerably from the actual ratio.

The guide wire 101 shown in FIG. 4 is a catheter guide wire for use in insertion into a catheter. The guide wire 1 has a core 102, a proximal tube 103 which is disposed on the proximal side of the core 102 and covers the proximal side of the core 102, and a helical coil 104. The proximal side of the core 102 is thinner than the distal side, with the proximal tube 103 being disposed so as to cover this thin portion (also referred to below as the "small diameter portion 110").

The guide wire 101 has a total length which, while not subject to any particular limitation, is preferably in a range of from about 200 mm to about 5,000 mm. The core 102 has an outer diameter (outer diameter of portion having a constant outer diameter) which, while not subject to any particular limitation, is preferably from about 0.1 mm to about 1.0 mm at the small diameter portion 110 on the proximal side, and is preferably from about 0.2 mm to about 1.2 mm in other portions on the distal side. The proximal tube 103 has an outer diameter which, while not subject to any particular limitation, is preferably from about 0.2 mm to about 1.2 mm. It is preferable for the inner diameter of the proximal tube 103 and the outer diameter of the small diameter portion 110 of the core 102 to be substantially the same and for the proximal tube 103 to be in close contact with the core 102.

At least the distal end of the core in the guide wire (B) is made of the ferrous alloy of the invention. In the present embodiment, all of the core 102 is a wire with elasticity that is made of the ferrous alloy of the invention. The core 102 has a length which, while not subject to any particular limitation, is preferably in a range of from about 200 mm to about 5,000 mm.

Also, in the present embodiment, apart from the small diameter portion 110 thereof, the core 102 has an outer diameter which is constant for a given length from the proximal end thereof, then tapers toward the distal end starting at some intermediate point. This latter portion is referred to herein as the tapering diameter portion 115. By having such a tapering diameter portion 115, the rigidity (flexural rigidity, torsional rigidity) of the core 102 can be gradually reduced in the distal direction. As a result, the guide wire 101 has a good flexibility in the distal portion, thus improving the safety and the ability of the guide wire to navigate a blood vessel, and preventing undesirable effects such as kinking.

In the illustrated arrangement, the tapering diameter portion 115 is formed as part of the core 102 outside of the small diameter portion 110, although the core 102 may be in its entirety a tapering diameter portion 115. The angle of taper (rate of reduction in the outer diameter) on the tapering diameter portion 115 may be constant along the length of the wire or there may be points along the length where the angle of taper changes. For example, a plurality of places where the angle of taper is relatively large and a plurality of places where the angle of taper is relatively small may be repeatedly formed in alternation.

Or the core 102 may have a portion with an outer diameter that is constant in the lengthwise direction, either partway along the tapering diameter portion 115 or distal to the tapering diameter portion 115. For example, the core 102 may have formed, at a plurality of places in the lengthwise direction, tapered portions on which the outer diameter tapers in the distal direction, and may have formed, between one such tapered portion and another such tapered portion, a portion having a constant outer diameter in the lengthwise direction. The effects achieved in such cases are the same as those indicated above.

Alternatively, unlike the arrangement shown in FIG. 4, it is possible for the guide wire 101 to have a configuration in which the proximal end of the tapering diameter portion 115 is situated partway along the proximal tube 103; i.e., the tapering diameter portion 115 is formed so as to straddle the interface between the core 102 and the proximal tube 103.

The material making up the core 102 is the ferrous alloy of the invention, which is described more fully later in the specification.

In the guide wire (B), when a portion of the core other than the distal portion is made of a material other than the ferrous alloy of the invention, the other material is not subject to any particular limitation. For example, the material may the same as that used in the subsequently described proximal tube 103.

The proximal side of the core 102 is covered by the proximal tube 103. The proximal tube 103 is composed of metal wire having a higher elasticity than the core 102. The proximal tube 103 has a length which, while not subject to any particular limitation, is preferably in a range of from about 20 mm to about 4,800 mm.

In FIG. 4, the core 102 has on the proximal side thereof the small diameter portion 110 which is covered by the proximal tube 103. However, in the guide wire (B), the core 102 need not necessarily have the small diameter portion 110. That is, the core 102 may have a portion other than the tapering diameter portion 115 which has an outer diameter that is constant, which outer diameter is substantially the same as the inner diameter of the proximal tube 103.

The proximal tube 103 is made of a material having larger moduli of elasticity (Young's modulus (longitudinal elastic modulus), modulus of rigidity (modulus of transverse elasticity), volumetric elastic modulus) than the material making up the core 102. In this way, a suitable rigidity (flexural rigidity, torsional rigidity) can be achieved in the proximal tube 103, giving the guide wire 101*a* good stiffness that enhances the pushability and torque transmission, enabling a better operability to be achieved during insertion.

The material making up the proximal tube 103 is not subject to any particular limitation, and may of the same type as the material making up the proximal core member 3 in the guide wire (A). Preferred examples of the material are the same as those mentioned above for the material used in the proximal core member 3 in guide wire (A). Alternatively, the material may be a cobalt alloy.

Preferred combinations of the core 102 and the proximal tube 103 are ones in which the core 102 is made of a ferrous alloy of the invention and the proximal tube 103 is made of a stainless steel or a cobalt alloy. The above-indicated effects can be more distinctly achieved in this way. Alternatively, bringing a pipe-shaped proximal tube made of an iron-containing material such as stainless steel into close contact with the proximal side of the core made of the ferrous alloy of the invention is desirable because the ability for the core and the proximal tube to mutually bond tends to increase as a result. The diffusion therebetween of iron present in the core and the proximal tube is thought to be an important factor in this effect.

The cobalt alloy referred to here has a high modulus of elasticity and a suitable elastic limit. The cobalt alloy used may be any alloy which contains cobalt as a constituent element, although the use of an alloy containing cobalt as a primary component (cobalt-based alloys refer herein to alloys in which, of the elements making up the alloy, the content of cobalt in terms of weight ratio is the highest) is preferred, and the use of a Co—Ni—Cr alloy is more preferred. Alloys having such a composition, when used as the material making up the proximal tube 103, render the above-described effects of the embodiment even more striking. Moreover, because alloys of such a composition have a plasticity even when deformed at room temperature, they can be easily deformed into a desired shape at the time of use, for example. Alloys with such a composition have a high coefficient of elasticity and are cold-formable even at a high elastic limit. Because of the high elastic limit, a smaller diameter can be achieved while fully preventing buckling from occurring. In addition, the alloy can be provided with a flexibility and a rigidity sufficient for insertion to the target site.

Preferred Co—Ni—Cr alloys include alloys having a composition which includes from 28 to 50 wt % cobalt, from 10 to 30 wt % nickel, and from 10 to 30 wt % chromium, with the balance being iron; and alloys in which a portion of the above has been substituted with other elements (substitution elements). The inclusion of substitution elements elicits effects that are specific to the particular elements. For example, by including one or more elements selected from among titanium, niobium, tantalum, beryllium and molybdenum as substitution elements, the strength of the proximal tube 103 can be improved even further. When an element other than cobalt, nickel and chromium is included, the content thereof (i.e., of the substitution elements overall) is preferably not more than 30 wt %.

It is also possible for portions of the cobalt, nickel and chromium to be substituted with other elements. For example, a portion of the nickel may be substituted with manganese to achieve, for example, a further improvement in workability. Also, a portion of the chromium may be substituted with molybdenum and/or tungsten so as to, for example, further improve the elastic limit. Of such Co—Ni—Cr alloys, the use of molybdenum-containing alloys, i.e., Co—Ni—Cr—Mo alloys, is especially preferred.

The Co—Ni—Cr alloys are exemplified by alloys having the following compositions (the numbers indicate percent by weight):

40Co-22Ni-25Cr-2Mn-0.17C-0.03Be-balance Fe
40Co-15Ni-20Cr-2Mn-7Mo-0.15C-0.03Be-balance Fe
42Co-13Ni-20Cr-1.6Mn-2Mo-2.8W-0.2C-0.04Be-balance Fe
45Co-21Ni-18Cr-1Mn-4Mo-1Ti-0.02C-0.3Be-balance Fe
34Co-21Ni-14Cr-0.5Mn-6Mo-2.5Nb-0.5Ta-balance Fe As used herein, "Co—Ni—Cr alloy" encompasses the above alloys.

In the illustrated arrangement, the proximal tube 103 has a substantially constant outer diameter over substantially its entire length, although it may have sites thereon where the outer diameter changes in the lengthwise direction.

The positioning, material and other features of the coil 104 may be the same as for the coil 4 in the above-described guide wire (A). Preferred features of the coil 104 are likewise the same as described for the coil 4 in guide wire (A).

In the guide wire 101 of the present embodiment, the core 102 and the proximal tube 103 are coupled (fixed) to each other by placing them together, then subjecting them to a drawing operation or the like. In this way, a high coupling strength (bond strength) can be achieved at the connection between the core 102 and the proximal tube 103, making it possible in the guide wire 101 for torsional torque and pushing force from the proximal tube 103 to be reliably transmitted to the core 102.

The core 102 (small diameter portion 110) and the proximal tube 103 may be joined together by spot-like laser welding to the outside surface of the proximal tube 103 or by welding in the lengthwise direction as in a seam pipe. This is preferable because the bondability between the core 102 and the proximal tube 103 can be enhanced. In cases where a proximal tube composed of stainless steel is used is in particular, this is even more preferable because the bondability is further enhanced. The reason is that, in the guide wire (B), the core 102 is made of the ferrous alloy of the invention. When the core is made of, unlike the guide wire (B), a Ti—Ni alloy for example, brittle intermetallic compounds composed of titanium and iron form at the joint between the proximal tube made of stainless steel and the core. In such a case, the bondability between the core and the proximal tube is low. In the guide wire (B), by using a proximal tube composed of stainless steel, such brittle intermetallic compounds do not readily form in the welded area, resulting in a strong bond.

The guide wire (B) has a coating 105 which covers part or all of the outside peripheral surface of the core 102 and the proximal tube 103. This coating 105 may be formed for various purposes, one example of which is to reduce friction (sliding friction) by the guide wire 101, improve slideability, and thereby improve the operability of the guide wire 101.

To this end, it is preferable for the coating 105 to be made of a material capable of reducing friction. Frictional resistance (sliding resistance) with the inside wall of the catheter used together with the guide wire 101 is thereby reduced, enhancing the slideability and thus resulting in a better guide wire 101 operability within the catheter. Moreover, because the sliding resistance of the guide wire 101 is lower, when the guide wire 101 is moved and/or rotated within the catheter, kinking and twisting of the guide wire 101, particularly kinking and twisting in the vicinity of the weld, can be reliably prevented.

Materials capable of being used as the coating 5 in the above-described guide wire (A) may be used as such friction-lowering materials in the present embodiment. The preferred examples of such materials mentioned above in connection with the guide wire (A) are preferable for use in the present embodiment as well.

The places where the coating 105 are formed and the thickness of the coating 105 are likewise the same as described above with regard to the coating 5 used in the earlier described guide wire (A).

In the guide wire (B), treatment (e.g., chemical treatment, heat treatment) for the purpose of improving adhesion of the coating 105 may be applied to the outer peripheral surface of the core 102 and/or the proximal tube 103. Alternatively, an intermediate layer capable of improving the adhesion of the coating 105 may be provided thereto.

Figure 5:
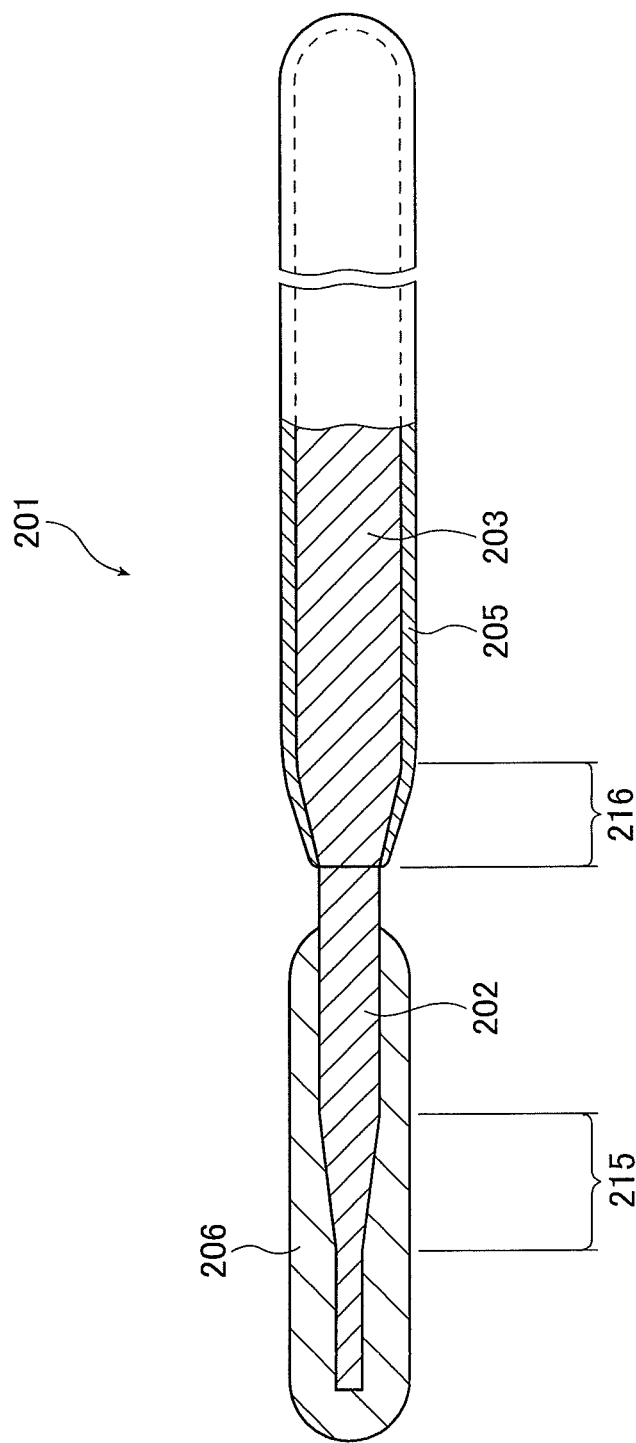
FIG. 5 is a longitudinal sectional view showing an embodiment of a guide wire (C) according to yet another aspect of the invention.

Next, an embodiment of a guide wire (C) is described while referring to FIG. 5, with particular reference to those features which differ from the foregoing embodiments of the guide wires (A) and (B). Descriptions of like features are omitted.

In a guide wire 201 shown in FIG. 5, a distal core member 202 and a proximal core member 203 are composed of ferrous alloys. At least part of the surface of the proximal core member 203 has a first coating 205 therein made of a fluorocarbon resin.

A second coating 206 differing from the first coating 205 is formed distal to the first coating 205. The first coating 205 is provided so as to cover all or part of the proximal core member 203. In the illustrated arrangement, the first coating 205 covers substantially all of the proximal core member 203.

The second coating 206 is provided so as to cover all or part of the distal core member 202. In the illustrated arrangement, the second coating 206 covers substantially all of the distal core member 202.

The first coating 205 is made of a fluorocarbon resin such as PTFE or PFA. In addition, a separate coating (undercoat) may be provided between the proximal core member 203 and the first coating 205. By having the undercoat be composed of a resin such as a polyimide, polyamide or polyamideimide which is capable of resisting even the melting temperature of the fluorocarbon resin, the resistance to separation (peel resistance) of the first coating 205 made of a fluorocarbon resin from the proximal core member 203 can be improved. Alternatively, the peel resistance between the first coating 205 and the undercoat can be improved by mixing a fluorocarbon resin such as PTFE and PFA into the undercoat. In this way, the proximal core member 203 made of a ferrous alloy having an extremely broad superelasticity region is capable of following twists and turns, along with which a good slideability can be achieved on account of the first coating 205 made of a fluorocarbon resin.

It is also possible to roughen the surface of the proximal core member 203 so as to improve the peel resistance of the first coating 205.

The second coating 206 is preferably made of a thermoplastic elastomer. Because the distal core member 202 is made of the subsequently described ferrous alloy, it can be deformed over a broader superelasticity region than Ti—Ni alloys. However, even when the distal core member made of the subsequently described ferrous alloy is subjected to a large deformation, because the second coating 206 is made of a thermoplastic elastomer, stretching by the coating conforms to deformation of the distal core member, as a result of which the coating does not readily peel from the distal core member.

Examples of the thermoplastic elastomer include polyurethane elastomers and polyamide elastomers. It is desirable for a hydrophilic material to be coated onto the outside surface of the second coating 206 made of a thermoplastic elastomer. In addition, to improve the peel resistance, it is possible to provide between the second coating 206 and the distal core member 202 a resin layer having a higher resistance to peeling from the distal core member 202 than the second coating 206. Also, the resistance of the coating 206 to peeling from the distal core member 202 can be improved by roughening the surface of the distal core member 202.

The first coating 205 has an average thickness which, while not subject to any particular limitation, is preferably from about 1 μm to about 20 μm, and more preferably from about 2 μm to about 10 μm.

The distal core member 202 has a tapering diameter portion 215, and the proximal core member 203 has a tapering diameter portion 216. The second coating 206 is coated to a uniform outer diameter along the length of the tapering diameter portion 215. The first coating 205 is coated to a substantially uniform diameter at the tapering diameter portion 216 and proximal thereto.

In an alternative arrangement, the second coating 206 on the guide wire (C) may cover the proximal core member 203. In such a case, the first coating 205 need not be provided. Even in such an arrangement, to further improve the peel resistance, it is possible to provide, between the second coating 206 and the proximal core member 203, a resin layer having a higher resistance to peeling from the proximal core member 203 than the second coating 206. Also, the peel resistance of the second coating 206 from the proximal core member 203 can be improved by roughening the surface of the proximal core member 203.

In the arrangement shown in FIG. 5, the distal end of the first coating 205 and the proximal end of the second coating 206 are located away from each other. However, the two layers may be formed so as to be continuous, or the first coating 205 and the second coating 206 may partially overlap.

Next, the stent according to further aspect of the present invention is described.

The stent has a body composed of the ferrous metal of the invention. For example, the stent body may have on the surface thereof (inside surface and/or outside surface) a film composed of a biocompatible material. Alternatively, a body alone that does not have such a film thereon is also acceptable and within the scope of the invention.

Next, the shape of the stent is described using preferred embodiments shown in the attached diagrams.

Figure 6:
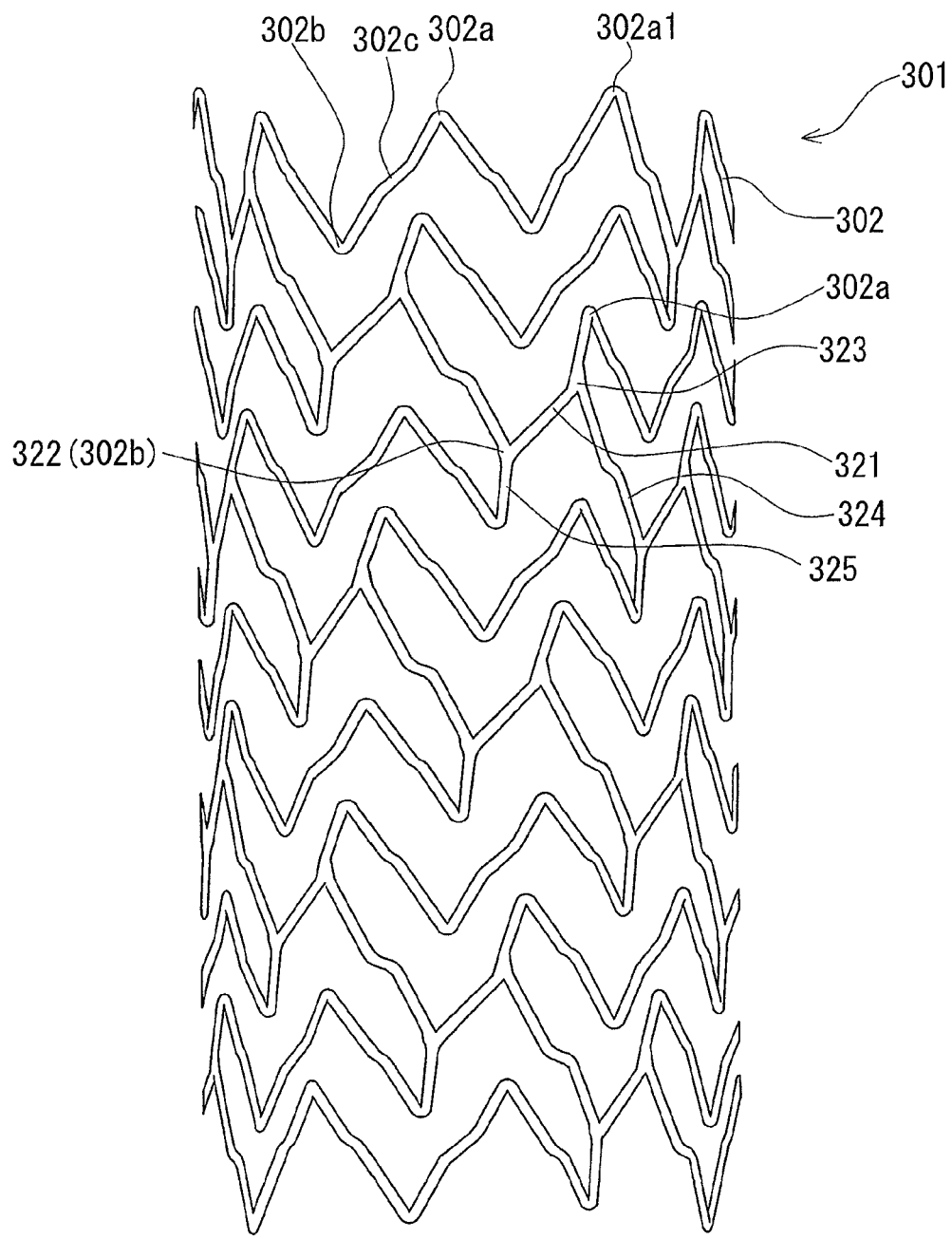
FIG. 6 is a front view of a stent according to Examples of the invention.
Figure 7:
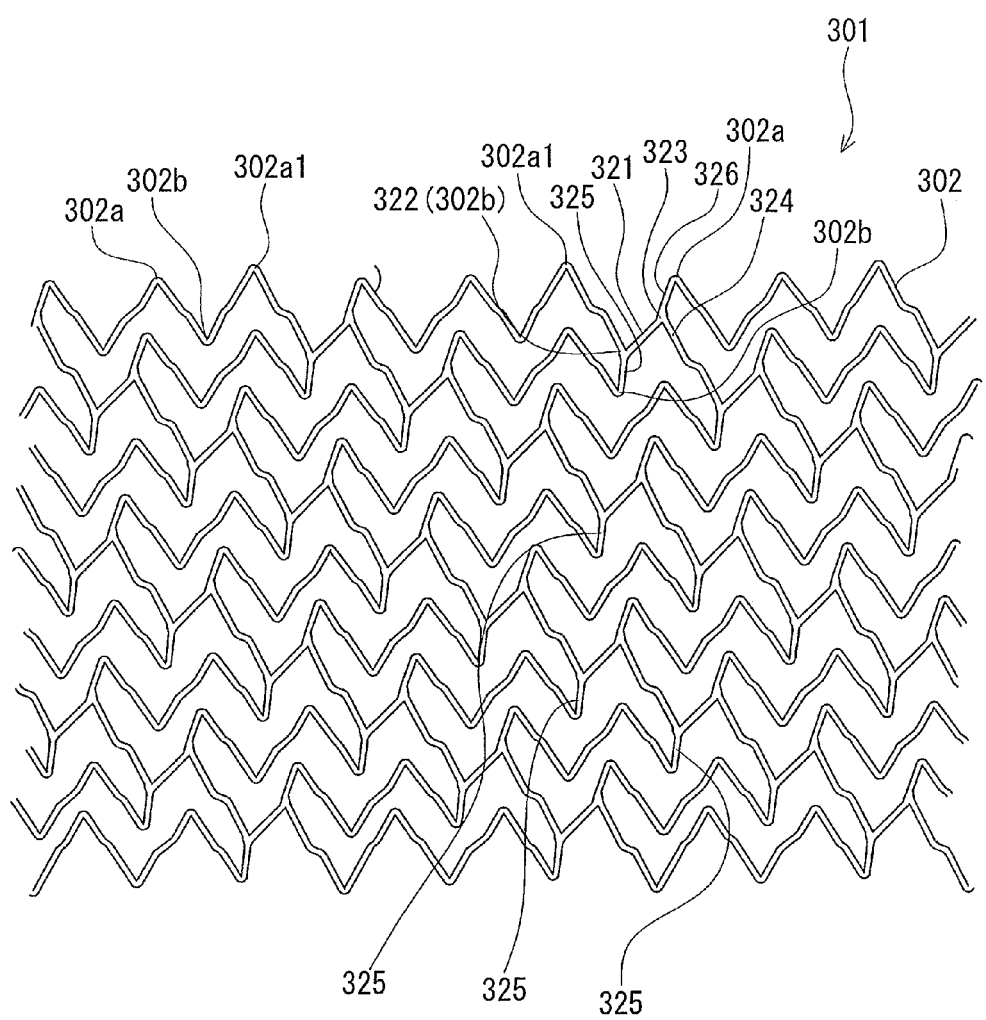
FIG. 7 is a development view of the stent shown in FIG. 6.
Figure 8:
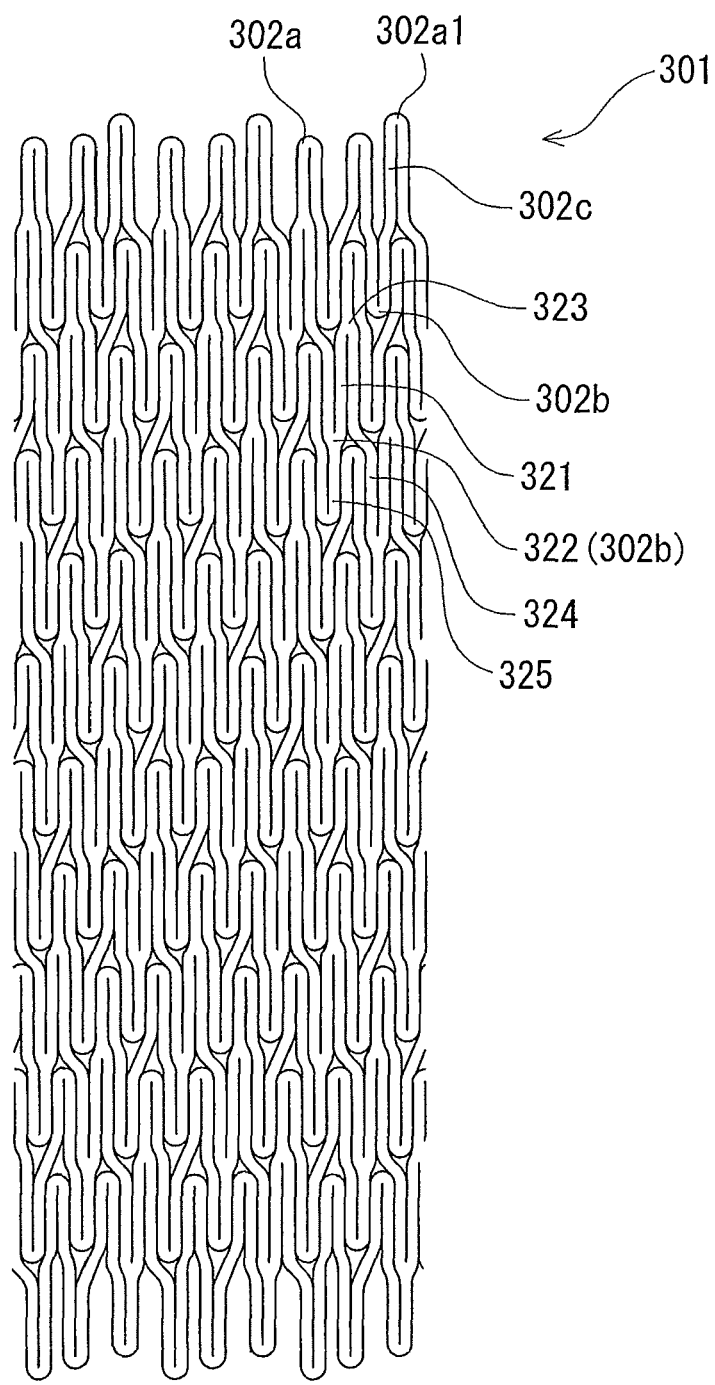
FIG. 8 is a development view of the stent shown in FIG. 6, in the contracted state.
Figure 9:
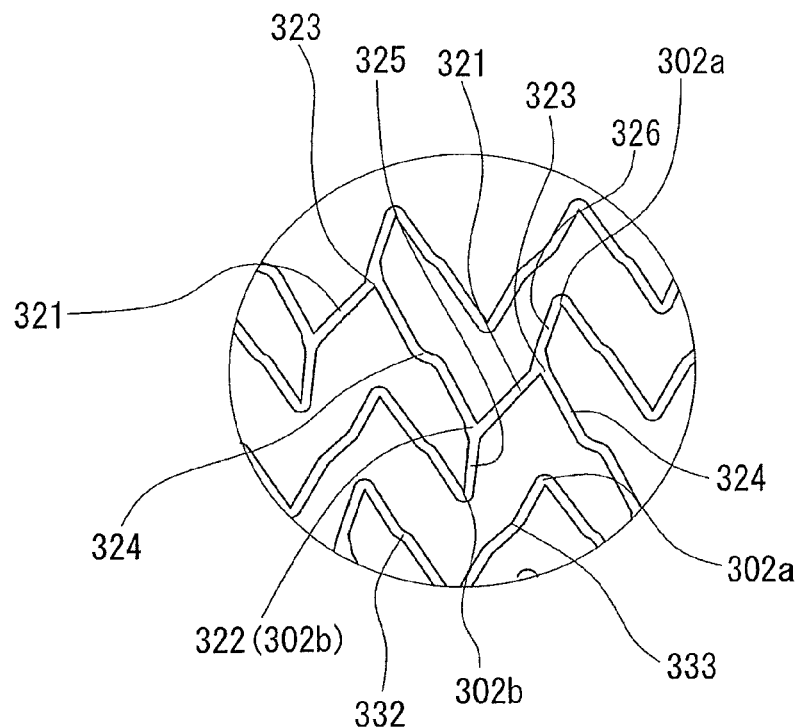
FIG. 9 is a partial, enlarged view of the stent shown in FIG. 6.

FIG. 6 is a front view showing the shape of a stent according to a preferred embodiment of the invention. FIG. 7 is a development view of the stent shown in FIG. 6. FIG. 8 is a development view of the stent shown in FIG. 6, in the contracted state. FIG. 9 is a partial, enlarged view of the stent shown in FIG. 6.

The stent 301 of the present embodiment is a stent having a plurality of undulating rings 302. Each undulating ring 302 has a plurality of first-side bends with an apex 302a on a first side in the axial direction of the stent 301, and a plurality of second-side bends with an apex 302b on a second side in the axial direction of the stent 301. Undulating rings 302 which are mutually adjacent in the axial direction of the stent 301 have a shared linear segment 321 which has a starting end 322 at or near one apex 302b of a second-side bend in the undulating ring 302 on the first side in the axial direction of the stent 301 and which has a terminal end 323 between the apex 302b in the second-side bend and an apex 302a in a first-side bend, which shared linear segment 321 unites the mutually adjoining undulating rings.

The stent has an arrangement which includes no elements provided solely as links and is composed solely of elements that effectively contribute a force of expansion, because it is made up of a plurality of rings in the form of mutually adjoining undulating rings that are united by the presence of partly shared segments.

The stent in the present embodiment is a so-called self-expanding stent which is formed in a substantially cylindrical shape, which is in a contracted state at the time of insertion into the body, and which, when it has been placed within the body, is capable of returning to its original expanded shape prior to contraction. FIG. 6 shows the appearance of the stent 301 when expanded.

In the stent shown in FIG. 6, the number of undulating rings 302 which form the stent 301 is eleven. The number of undulating rings 302 differs depending on the length of the stent, but is preferably from 2 to 150, and more preferably from 5 to 100.

Each undulating ring 302 has a plurality of first-side bends having an apex on a first side in the axial direction of the stent 301 and a plurality of second-side bends having an apex on a second side in the axial direction of the stent 301, and is composed of an endless undulating element which is annularly continuous. The first-side bends and the second-side bends in the ring 302 are alternately formed, and thus are each present in the same number. In the stent shown in FIG. 6, the number of first-side bends (second-side bends) in a single undulating ring 302 is nine. The number of first-side bends (second-side bends) is preferably from 4 to 20, and more preferably from 6 to 12. Moreover, the linear elements which form the annular ring 302 in the stent of the present embodiment are almost always curved; rectilinear elements are very rare. Because the linear elements forming the ring 302 thus have a sufficient length, a large expansion force acts during expansion. The undulating ring 302 has a length in the axial direction of preferably from 1 to 10 mm, and more preferably from 1.5 to 5 mm.

In the stent 301 of the present embodiment, as shown in FIGS. 6 to 9, each of the undulating rings 302 has a large wave that forms a salient first-side apex 302a1 which projects out further on the first side than the apices 302a on other first-side bends, and that forms a salient second-side apex (which, in the present embodiment, coincides with a starting end) 322 which projects out further on the second side than the apices of the other second-side bends. Moreover, in the present embodiment, the undulating rings each have a plurality of large waves. In the present stent, one ring has nine first-side bends, and three large waves are provided within a single ring. The three large waves are formed so as to be spaced apart at substantially equal angles with respect to the center axis of the stent 301.

Undulating rings 302 which are mutually adjacent in the axial direction of the stent 301 have a shared linear segment 321 with a starting end 322 at or near one apex 302b of a second-side bend in the undulating ring 302 on the first side of the stent 301 in the axial direction thereof and having a terminal end 323 between the apex 302b in the second-side bend and an apex 302a in a first-side bend on the same ring 302, which shared linear segment 321 unites the mutually adjacent undulating rings.

Specifically, the shared linear segment 321 has, as the starting end 322 thereof, one apex 302b on a second-side bend in an annular ring 302 on a first side of the stent 301 in the axial direction thereof. The starting end 322 and the apex 302b are the same. The shared linear segment 321 has a terminal end 323 located between the foregoing apex 302b (which is also the starting end 322) and the apex 302a of a first-side bend that is continuous thereto. In particular, in the present embodiment, the shared linear segment 321 has a terminal end 323 located substantially near the midpoint between the foregoing apex 302b (which is also the starting end 322) and the apex 302a of the first-side bend that is continuous thereto. The terminal end 323 is preferably located at the midpoint, although it may be located at any apex-side position from about $1/100$ to about $49/100$ of the total length between the foregoing apex 302b (which is also the starting end 322) and the apex 302a of the first-side bend that is continuous thereto. In the present embodiment, the terminal end 323 is preferably positioned somewhat to the apex 302a side from the midpoint.

The stent 301, owing to the above-described arrangement, has a starting end branch which forms the starting end site for the shared linear segment 321 and has a terminal end branch which forms the terminal end site for the shared linear segment 321. Specifically, the starting end branch has a shape which divides into two legs facing the first side at the starting end 322 as the branch point, and the terminal end branch has a shape which divides into two legs facing the second side at the terminal end 323 as the branch point.

Moreover, in the stent 301 of the present embodiment, the interval between the salient first-side apex 302a1 and the salient second-side apex (which is the same as the starting end 322) in a large wave is a linear segment which is longer than connecting linear segments between other apices. As noted above, the second-side end of this long linear segment is the starting end of the shared linear segment. It should also be noted that, in the present embodiment, the shared linear segment 321 is formed on part of a large wave.

In the stent 301 of the present embodiment, as shown in FIG. 7, each undulating ring 302 has a short linear segment 326 which connects between the terminal end 323 of the shared linear segment 321 and the apex 302a of a first-side bend. Moreover, as shown in FIG. 7, the ring 302 which is united by the shared linear segment 321 with the ring 302 having the above short linear segment 326 has a short linear segment 325 which connects between the starting end 322 of the shared linear segment 321 and the apex 302b of a second-side bend and has a long linear segment 324 which connects between the terminal end 323 of the shared linear segment 321 and another apex 302b of a second-side bend. Therefore, the interval between the salient first-side apex (which is the same as the terminal end 323) on a large wave and a salient second-side apex (which coincides with the starting end 322 of the linear segment shared with the adjoining ring on the second side) forms a long linear segment. That is, in the present stent 301, shared linear segments 321 which are mutually adjoining in the axial direction have a configuration wherein, as viewed from the first side of the stent 301 in the axial direction, the terminal end 323 of one shared linear segment 321 and the starting end 322 of the other shared linear segment 321 adjacent thereto are connected by a long linear segment 324. Accordingly, as shown in FIG. 7, in the present stent 301, a zigzag arrangement composed of repeated long linear segments 324 and shared linear segments 321 forms a helix that extends from one end to the other end of the stent 301.

Moreover, because this stent has no so-called links, there are no obstacles to curvature or decreases in expansion force caused by such links. As a result, the entire stent exhibits a uniform expansion retaining force.

Also, the stent 301 of the present embodiment has a plurality of shared linear segments 321 between mutually adjacent undulating rings. Specifically, three shared linear segments 321 are provided between mutually adjacent undulating rings. Moreover, the three shared linear segments 321 are formed at intervals that are spaced at substantially equal angles with respect to the center axis of the stent 301.

Furthermore, in the stent 301 of the present embodiment, short linear segments 325 which connect between the starting ends 322 of the shared linear segments 321 and the apices 302b of second-side bends, are not continuous in the axial direction of the stent 301, and a plurality of the short linear segments 325 are formed so as to be substantially rectilinear. Also, in the stent 301 of the present embodiment, linear segments other than the above-described short linear segments 325 and 326 (i.e., long linear segments and other linear segments) have near the center thereof, as shown in FIG. 9, areas of inflection 332 where the linear segment advances in a direction that changes somewhat while remaining substantially parallel. Such areas of inflection 332 increase the length of the linear segments and also increase the expansion force.

Also, in the stent 301 of the present embodiment, the long linear segments 324 have a length (i.e., the length between the terminal end 323 of a shared linear segment 321 and the starting end 322 of another shared linear segment 321) which is somewhat longer than the combined length of a shared linear segment 321 and a short linear segment 325 (i.e., the length from the terminal end 323 of the shared linear segment 321 to the apex 302b beyond the starting end 322 thereof). This makes it possible to prevent the apex 302b from coming too close to the linear segment 333 of an adjoining ring (specifically, an ordinary linear segment which connects one apex 302a with another apex 302b, and which has no shared linear segment and no branch point), enabling deviations in width within the closed spaces formed by linear segments (in the present embodiment, the closed spaces formed by connecting the "V" and "M" shapes, as shown in FIG. 7) to be minimized, so that a high expansion holding force is achieved.

Also, as shown in FIG. 7, the apices 302a of first-side bends in the undulating rings 302 intrude on the spaces that form between the apices 302b of second-side bends on one of the neighboring undulating rings, and the apices 302b of the second-side bends in the undulating rings 302 intrude on the spaces that form between the apices 302a of first-side bends on the other neighboring undulating ring. This arrangement enables the length of the linear segments making up the stent to be increased, and also makes it possible to reduce the surface areas of the closed spaces formed by the linear segments (in the present embodiment, the closed spaces formed by connecting the "V" and "M" shapes, as shown in FIG. 7), enabling a higher expansion holding force to be achieved.

Furthermore, in the stent 301 of the present embodiment, when the stent 301 is in the contracted state shown in FIG. 8, the various elements are arranged with substantially no intervening gaps in the circumferential direction. As a result, the stent 301 has a high coverage.

The stent has the shape, for example, as described above.

In cases where the stent has a shape like that described above and the body is made of the ferrous alloy of the invention, even after placement of the stent in vasculature subject to large deformation, such as in the legs, the stent does not fail due to large deformation and moreover has an excellent durability (fatigue strength).

Although the stent will have a size which varies depending on the site where it is to be placed, the outer diameter of the stent when expanded (i.e., when restored to the original shape and no longer contracted) is preferably from 2.0 to 30 mm, and more preferably from 2.5 to 20 mm. The stent length is preferably from 10 to 150 mm, and more preferably from 15 to 100 mm. In particular, a stent according to the embodiment that is intended for placement within a blood vessel will have an outer diameter of preferably from 2.0 to 14 mm, and more preferably from 2.5 to 12 mm, and a length of preferably from 5 to 100 mm, and more preferably from 10 to 80 mm.

The stent may have a wall thickness that is smaller than in conventional stents. The body of the stent, because it is formed of the subsequently described ferrous alloy of the invention, has a high strength and durability. Accordingly, even at a small wall thickness, the stent will possess the desired strength and durability. For example, the wall thickness may be set to 0.2 mm or less, or even 0.10 mm or less.

The body of the stent may be fabricated by using a pipe made of the ferrous alloy of the invention and removing (such as by cutting or melting away) those portions of the pipe that do not form a part of the stent. In this way, an integral structure is obtained. A pipe used to form the body of the stent can be manufactured by melting the ferrous alloy of the invention in an inert gas or evacuated atmosphere to form a ferrous alloy ingot, mechanically grinding the ingot, then hot pressing and extruding to form a large-diameter pipe. Successive die drawing steps and heat treatment steps are then carried out repeatedly to reduce the pipe to a given wall thickness and outer diameter, after which the surface of the resulting pipe is chemically or physically polished. The stent base material can be formed from the pipe by a suitable process such as cutting (e.g., mechanical grinding, laser cutting), electrical discharge machining, chemical etching, or a combination of such techniques.

The body of the stent is preferably made of braided wire, because an indwelling stent made of braided wire readily conforms to bodily movement and vascular pulsation.

After it has been fashioned to the final shape of the stent, the body of the stent is preferably subjected to solution treatment at from 900 to 1400° C., rapidly cooled at a rate of at least 50° C./s, then aged at a temperature of at least 200° C. but less than 800° C. By carrying out such solution treatment and aging treatment, the superelasticity and strength of the stent body are improved, thereby enhancing the flexibility of the entire stent body, resulting in good ease of placement within tortuous blood vessels.

The diameter of the stent when unexpanded is preferably from about 0.8 mm to about 1.8 mm, and more preferably from about 0.9 mm to about 1.6 mm. The length of the stent when unexpanded is preferably from about 10 mm to about 200 mm. The length of a single undulating ring is preferably from about 8 mm to about 40 mm.

Although stents are generally provided with imaging markers, the stents according to the present embodiment need not be provided with such markers because, as noted above, the ferrous alloys of the invention used in the stents have excellent fluoroscopic visualization properties.

Next, the ferrous alloys of the invention are described.

1. Crystal Structure and Properties of Ferrous Alloy

Figure 10:
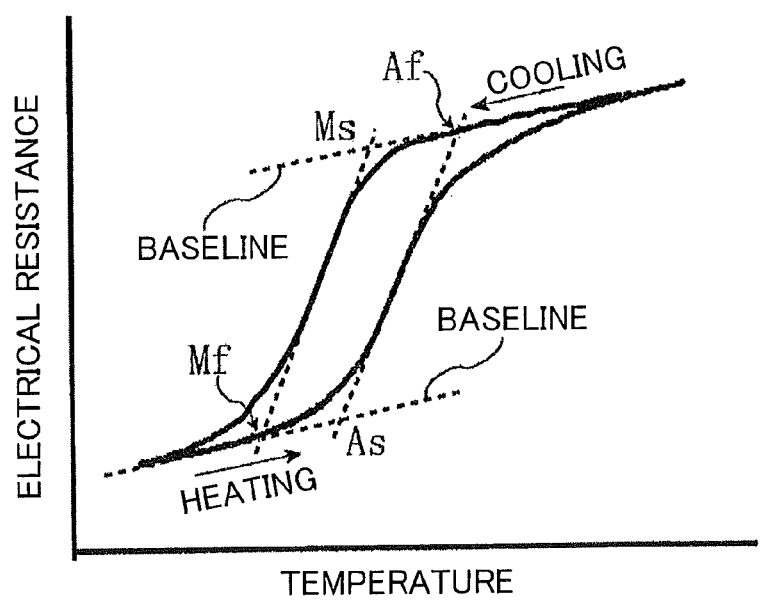
FIG. 10 shows a typical electrical resistance curve for a shape-memory alloy (the martensitic transformation start temperature (Ms point) and the reverse transformation finish temperature (Af point) can be determined from an electrical resistance curve of the martensitic transformation in cooling and the reverse transformation in heating)

The ferrous alloys of the invention have what is substantially a dual-phase structure composed of a γ phase having a face-centered cubic (fcc) structure serving as the matrix within which is finely dispersed a γ' ordered phase having a $L1_2$ structure. Cooling the γ phase induces a martensitic transformation to an α' phase having a body-centered cubic (bcc) structure, and heating once more brings about a reverse transformation to the matrix γ phase. The martensitic transformation start temperature (Ms point) and the reverse transformation finish temperature (Af point) can be determined by electrical resistance measurement. As shown in FIG. 10, in shape memory alloys, there is generally a hysteresis between the martensitic transformation and the reverse transformation.

Superelasticity in shape-memory alloys arises due to stress-induced martensitic transformations at and above the Af point and to the reverse transformations. However, if the hysteresis width is large, a high stress is required to induce the martensitic transformation, which tends to result in the introduction of permanent strain such as dislocations, preventing a good superelasticity from being achieved. Therefore, by making the hysteresis width smaller, a martensitic transformation can be induced at a lower stress, enabling good superelasticity to be achieved without the introduction of permanent strain such as dislocations at the time of deformation. As a result of extensive research, the inventors have found that the width of the thermal hysteresis for the ferrous alloys of the invention must be set to 100° C. or below to achieve such superelasticity. The width of the thermal hysteresis is preferably 70° C. or less.

It is preferable for the ferrous alloys of the invention to have a recrystallization texture in which the specific crystal orientation <100> or <110> of the matrix γ phase is aligned with the cold working direction (e.g., rolling, wire drawing). The ferrous alloys of the invention are able to achieve shape memory and superelastic properties even if the crystal orientations are completely random, although by having the foregoing specific crystal orientations aligned with the working direction, even better shape memory and superelastic properties may be achieved. Crystal orientations in the alloy texture can be measured by the electron backscatter diffraction pattern method and are expressed herein as the "abundance," which indicates the degree of alignment by the crystal orientation. The abundance of the crystal orientation <100> in the cold-working direction is a ratio based on an arbitrary value of "1" when the crystal orientation is completely random. A higher value indicates greater alignment of the crystal orientation.

The abundance of a specific crystal orientation in the working direction for the ferrous alloys of the invention is preferably at least 2.0, and more preferably at least 2.5.

The ferrous alloys of the invention which have a thermal hysteresis of 100° C. or less and wherein, moreover, the crystal orientations in the matrix γ phase are aligned have a higher Young's modulus and strength and a larger superelastic strain than Ti—Ni alloys. The Young's modulus is at least about 40 GPa, the 0.2% yield strength is at least about 600 MPa, and the superelastic strain is at least 5%. In addition, the ferrous shape-memory alloys of the invention are endowed with a good hardness, tensile strength and elongation at break, and thus have an excellent workability.

2. Composition of Ferrous Alloys (a) Basic Composition

The ferrous alloys of the invention have a basic composition which includes from 25 to 35% by mass of nickel, from 10 to 30% by mass of cobalt, and from 2 to 8% by mass of aluminum. In addition, the basic composition also includes a total of from 1 to 20% by mass of at least one selected from the group consisting of from 1 to 5% by mass of titanium, from 2 to 10% by mass of niobium, and from 3 to 20% by mass of tantalum. The balance is iron and inadvertent impurities. In the explanation provided herein of the ferrous alloy of the invention, unless noted otherwise, the contents of the respective elements are based on the overall alloy (100% by mass).

The ferrous alloy of the invention includes preferably at least 30% by mass and more preferably at least 35% by mass of iron. The ferrous alloy includes preferably not more than 55% by mass and more preferably not more than 50% by mass of iron. Iron is preferably contained in a range of from 30 to 55% by mass, and more preferably from 35 to 50% by mass. A too low content of iron in the ferrous alloy of the invention tends to lower the cold workability and further toughness following the treatment for imparting superelasticity (aging treatment). On the other hand, a too high iron content tends to increase the transformation hysteresis in fcc to bcc martensitic transformation (to have a temperature of 100° C. or higher), thus making it impossible to achieve good superelasticity.

Nickel is an element which induces a martensitic transformation and also lowers the temperature thereof. The ferrous alloy of the invention preferably includes from 25 to 35% by mass of nickel. By having a nickel content within this range, the martensitic transformation temperature of the ferrous alloy decreases, stabilizing the matrix phase (fcc phase). At a nickel content of more than 35% by mass, an excessive decline occurs in the martensitic transformation temperature and transformation does not arise within a practical temperature range, as a result of which a good shape memory effect and good superelasticity cannot be achieved.

In addition, nickel is an element which, in aging treatment, causes the precipitation of ordered phases having an fcc and/or fct structure, such as $Ni_3Al$. Such ordered phases strengthen the matrix phase of the ferrous alloy, in addition to which they reduce the thermal hysteresis of martensite, thereby enhancing the shape memory properties and the superelasticity. When the nickel content is less than 25% by mass, the amount of ordered phase that precipitates is insufficient, as a result of which good shape memory properties and superelasticity are not achieved. The nickel content is more preferably from 26 to 30% by mass.

Cobalt is an element which lowers the modulus of rigidity of the matrix phase and reduces transformation strain, thus improving the shape memory properties. It is preferable for the inventive ferrous alloy to include from 10 to 30% by mass of cobalt. At a cobalt content above 30% by mass, the cold workability of the alloy may decrease. At a cobalt content below 10% by mass, the above-indicated effects of cobalt added may not be fully achieved. The cobalt content is more preferably from 15 to 23% by mass.

Aluminum is an element which, as with nickel, induces the precipitation of fcc and/or fct γ' ordered phases of $Ni_3Al$ or the like in aging treatment. At an aluminum content below 2% by mass, the amount of ordered phase that precipitates is inadequate, thus making it impossible to achieve good shape memory properties and superelasticity. On the other hand, at an aluminum content above 8% by mass, the ferrous alloy becomes very brittle. The ferrous alloy of the invention has an aluminum content of preferably from 2 to 8% by mass, and more preferably from 4 to 6% by mass.

It is preferable for the ferrous alloy to additionally include a total of from 1 to 20% by mass of at least one primary added element selected from the group consisting of from 1 to 5% by mass of titanium, from 2 to 10% by mass of niobium, and from 3 to 20% by mass of tantalum. By including a primary added element, the amount of precipitation of the γ' ordered phase greatly increases, along with which the strength of the matrix phase rises considerably and the thermal hysteresis of martensite decreases markedly, resulting in improvements in the shape memory properties and the superelasticity. At a total content of these elements in excess of 20% by mass, the cold workability of the alloy may decrease.

(b) Other Elements

The ferrous alloys of the invention may also include at least one secondary added element selected from the group consisting of boron, carbon, calcium, magnesium, phosphorus, zirconium, ruthenium, lanthanum, hafnium, lead and misch metal. The total content of secondary added elements is preferably 1% by mass or less, more preferably from 0.001 to 1% by mass, and most preferably from 0.002 to 0.7% by mass. The secondary added elements suppress grain boundary reactions of β phase having a B2 structure which arise during aging, thereby improving the shape memory properties and the superelasticity.

The ferrous alloy of the invention may also include at least one tertiary added element selected from the group consisting of beryllium, silicon, germanium, manganese, chromium, vanadium, molybdenum, tungsten, copper, silver, gold, gallium, platinum, palladium, and rhenium. The total content of tertiary added elements is preferably 10% by mass or less, more preferably from 0.001 to 10% by mass, and most preferably from 0.01 to 8% by mass.

Of the tertiary added elements, silicon, germanium, vanadium, molybdenum, tungsten, gallium and rhenium increase coherence between the matrix γ phase and the γ' ordered phase, enhances precipitation strengthening of the γ' phase, and improves the shape memory properties. The total content of these elements is preferably 10% by mass or less.

Beryllium and copper improve the strength of the matrix γ phase due to solid solution strengthening, enhancing the shape memory properties. The contents of beryllium and copper are each preferably 1% by mass or less.

Chromium is an element which is effective for maintaining the wear resistance and corrosion resistance. The content of chromium is preferably 10% by mass or less.

Manganese lowers the Ms point, thus making it possible to lower the content of costly nickel. The content of manganese is preferably 5% by mass or less.

Silver, gold, platinum and palladium have the effect of increasing the tetragonal character of α' martensite, thus reducing the thermal hysteresis and improving the shape memory properties and the superelasticity. The content of these elements is preferably 10% by mass or less.

3. Method of Producing the Ferrous Alloy (a) Cold Working

The inventive ferrous alloy having the above composition is formed into the desired shape by melt casting, hot working and cold working. Solution treatment and aging are carried out following the shaping operations. The shaping operation carried out prior to solution treatment is preferably a cold working process such as cold rolling, cold wire drawing or die pressing. Cold working is preferred because, following solution treatment, there can be obtained a recrystallization texture in which specific crystal orientations of the γ phase are aligned in the cold working direction. A larger superelastic strain can be obtained in plates, pipes, wire and other worked materials having such a texture than in materials having random orientations. Moreover, after cold working, surface working such as shot peening may be carried if necessary. Hence, cold working enables plate, pipe, wire and other worked materials to be obtained in which specific crystal orientations of the γ phase are aligned with the working direction.

Because the reduction ratio (also referred to herein as the "working ratio") that can be achieved in the ferrous alloy by a single cold working pass is only about 10%, to achieve a high total reduction ratio in cold working, it is necessary to carry out a number of cold working passes. Cold working at this time may be carried out while interspersing a plurality of annealing treatment operations, in which case making the total reduction ratio after the final annealing operation as high as possible is desirable for increasing the orientation of the alloy texture. Annealing treatment preferably involves heating at a temperature of from 900 to 1300° C. for a period of from 1 minute to 3 hours. Cooling after annealing is preferably carried out by air cooling, and more preferably carried out by water cooling.

In the ferrous alloy of the invention, by means of cold working, the <100> or <110> orientation of the γ phase following solution treatment can be aligned with the cold working (e.g., rolling or wire drawing) direction. Crystal orientations in the alloy texture can be measured by the electron backscatter diffraction pattern method, and the results used to determine the "abundance," which indicates the degree of alignment of the crystal orientations. For example, the abundance of <100> in the working direction is a ratio based on an arbitrary value of "1" for the theoretical case in which the crystal orientations are completely random. A higher abundance value indicates greater uniformity of the crystal orientations.

As a result of extensive investigations, the inventors have found that when the abundance of a specific crystal orientation, such as <100> or <110>, of the γ phase is 2.0 or more, ferrous alloys having excellent shape memory properties and superelasticity can be obtained. In the ferrous alloys of the invention, the abundance of the above specific crystal orientation can be set by means of the total reduction ratio after the final annealing operation. To increase the abundance of the above specific crystal orientation, it is preferable for the total reduction ratio following the final annealing operation to be as high as possible. For this value to be 2.0 or more, regardless of the alloy composition, the total reduction ratio in cold working after the final annealing operation must be set to at least 50%. If the total reduction ratio in cold working after the final annealing operation is low, the specific crystal orientations in the alloy texture will not align with the working direction, making it impossible to achieve sufficient improvements in the shape memory properties and the superelasticity. The total reduction ratio in cold working is preferably at least 70%, and more preferably at least 92%.

(b) Solution Treatment

The cold-worked ferrous alloy is heated to the solid solution temperature and the crystal structure is transformed to an austenitic γ phase (single phase), after which it is preferable to carry out solution treatment involving rapid cooling. Solution treatment is carried out at a temperature of at least 800° C. The solution temperature is preferably from 900 to 1400° C. The holding time at the treatment temperature is preferably from 1 minute to 50 hours. At less than 1 minute, a sufficient solution treatment effect cannot be achieved, whereas at more than 50 hours, the influence of oxidation becomes impossible to disregard.

Solution treatment may be carried out while applying a stress. By carrying out such "tension annealing," the memory shape of the ferrous alloy can be precisely controlled. When stress is applied during solution treatment, the stress is preferably from 0.1 to 50 kgf/mm².

Following heat treatment, the γ single phase state can be frozen by quenching at a rate of at least 50° C./s. Quenching may be carried out by placing the ferrous alloy in a coolant such as water or by forced air cooling. When the cooling rate is set to less than 50° C./s, β phase (β phase having a B2 structure) precipitation occurs, as a result of which shape memory properties may not be achieved. The cooling rate is preferably at least 50° C./s.

(c) Aging Treatment

Following solution treatment, it is desirable to carry out aging treatment. By carrying out aging treatment, an ordered phase of $Ni_3Al$ or the like having a fcc and/or fct structure appears, strengthening the matrix phase and reducing the thermal hysteresis of martensitic transformation, thereby improving the shape memory properties and superelasticity. Aging treatment is carried out at a temperature of at least 200° C. but less than 800° C. Treatment at less than 200° C. results in insufficient precipitation of the above-mentioned ordered phase. On the other hand, treatment at 800° C. or above is undesirable because precipitation of the stable β phase occurs.

The aging treatment time varies depending on the ferrous alloy composition and the treatment temperature. When treatment is carried out at a temperature of at least 700° C. but less than 800° C., the aging treatment time is preferably in a range of from 10 minutes to 50 hours. On the other hand, when treatment is carried out at a temperature of at least 200° C. but less than 700° C., the aging treatment time is preferably in a range of from 30 minutes to 200 hours. When the aging treatment time is shorter than the above-indicated time, the resulting effects are inadequate. On the other hand, when the aging treatment time exceeds the above-indicated time, β phase precipitation may occur, resulting in a loss of the shape memory properties.

EXAMPLES

The ferrous alloys of the invention are illustrated more fully below by way of examples, although the invention is not limited by the examples.

Examples 1 to 5, and Comparative Example 1

The ferrous alloys of Examples 1 to 5 and Comparative Example 1, which are alike with the exception of the alloy compositions and the aging treatment times, were produced by the method described below.

Figure 11A:
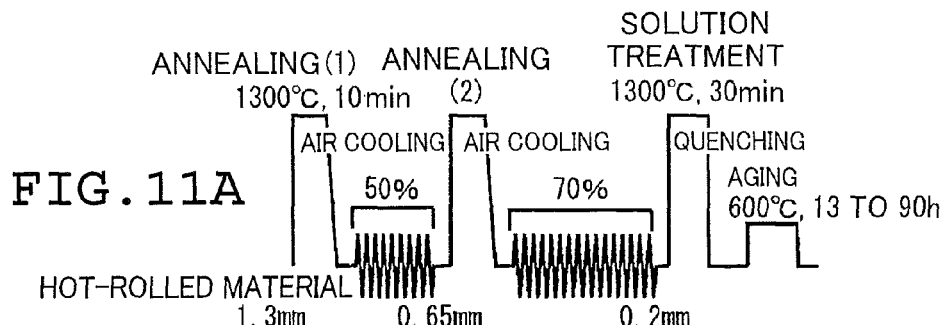
FIGS. 11A-11E are schematic diagrams showing examples of the sequence of operations from first annealing to aging in the production of ferrous alloys in Examples 1 to 5 of the invention and Comparative Example 1 (FIG. 11A), and in Examples 6 to 9 of the invention (FIGS. 11B to 11E)

In the respective examples, an alloy having the composition shown in Table 1 below was melted, then solidified at an average cooling rate of 140° C./min to form a billet having a diameter of 12 mm. The billet was hot-rolled at 1300° C., giving a 1.3 mm thick plate. The hot-rolled plate was then subjected to a first annealing operation at 1300° C. for 10 minutes, after which cold rolling was carried out several times to a plate thickness of 0.65 mm. A second annealing operation was then carried out under the same conditions, then cold rolling was carried out several times to give a 0.2 mm thick plate. The total reduction ratio after second annealing (final annealing) was 70%. The plate in each example was subsequently heat-treated at 1300° C. for 30 minutes, then plunged into ice water and thereby quenched (solution treatment). Next, aging treatment at 600° C. was carried out, thereby giving a ferrous alloy plate which was composed of two phases—a γ phase having an fcc structure and a γ' phase having a $L1_2$ structure, and which had shape memory properties and superelasticity. The production process, from the first annealing operation described above to aging treatment, is schematically shown in FIG. 11A. The aging treatment times for each alloy are shown in Table 1.

Examples 6 to 9

The ferrous alloys of Examples 6 to 9 are alloys which have the same composition but for which the process conditions from the annealing to the aging treatment operations differ. For example, the ferrous alloy of Example 6 was produced by the following method.

Figure 11B:
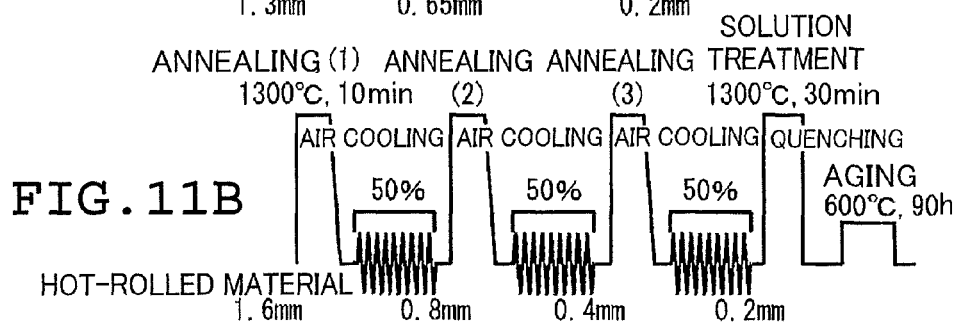

The alloy having the composition shown in Table 1 below was melted, then solidified at an average cooling rate of 140° C./min to form a billet having a diameter of 20 mm. The billet was hot-rolled at 1300° C., giving a 1.6 mm thick plate. The hot-rolled plate was then subjected to a first annealing operation at 1300° C. for 10 minutes, after which cold rolling was carried out several times to a plate thickness of 0.8 mm. Next, the following operations were carried out under the same conditions: second annealing→cold rolling→third annealing→cold rolling, yielding a 0.2 mm thick plate. The total reduction ratio after third annealing (final annealing) was 50%. The resulting plate was subsequently heat-treated at 1300° C. for 30 minutes, then plunged into ice water and thereby quenched (solution treatment). Next, aging treatment at 600° C. was carried out for 90 hours, thereby giving a ferrous alloy plate which was composed of two phases—a γ phase having an fcc structure and a γ' phase having a $L1_2$ structure, and which had shape memory properties and superelasticity. The process for producing the alloy of Example 6, from the first annealing operation described above to aging treatment, is schematically shown in FIG. 11B.

Figure 11C:
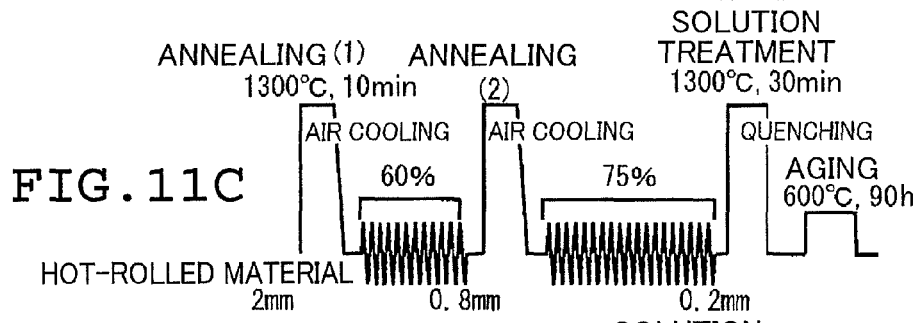
Figure 11D:
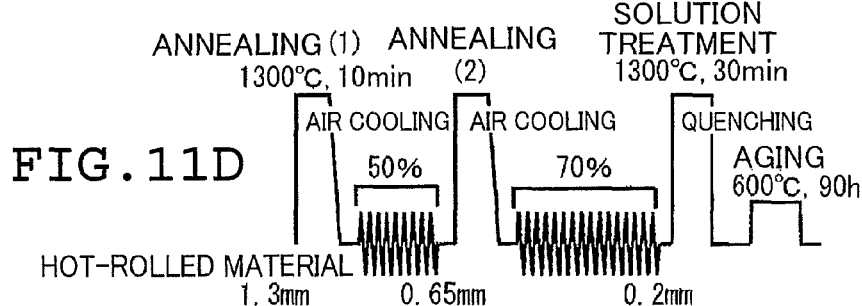
Figure 11E:
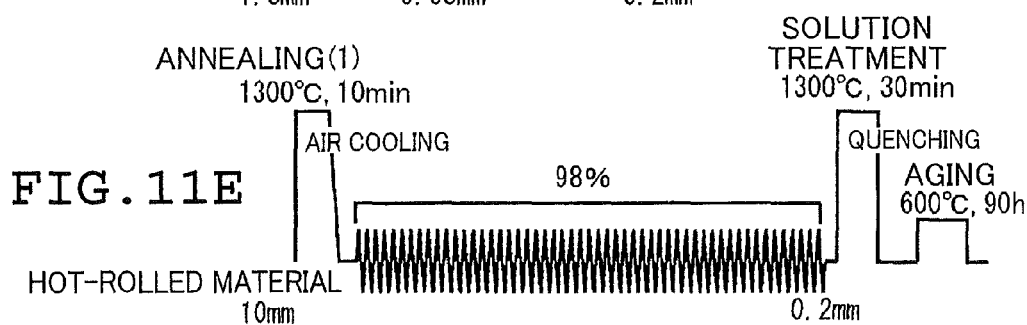

The ferrous alloys in Examples γ to 9 were produced by changing the sequence of annealing and cold rolling operations used to produce the ferrous alloy of Example 6 in the manner shown in FIGS. 11C to 11E. FIG. 11C relates to Example 7, FIG. 11D relates to Example 8, and FIG. 11E relates to Example 9. The total cold working ratios after the final annealing operation are shown in Table 1.

TABLE 1

| Ex. No | Fe | Ni | Co | Al | Ti | Nb | Ta | Other elements | Cold working ratio after final annealing (%) | Aging treatment time (h) | Young's modulus (Ga) | 0.2% Yield strength (MPa) | Superelastic strain | Difference between Af point and Ms point (° C.) | Abundance of <100> in rolling direction |
|---|---|---|---|---|---|---|---|---|---|---|---|---|---|---|---|
| EX 1 | 46.4 | 30.7 | 14.9 | 5.8 | 2.2 | | | | 70 | 48 | 76 | 630 | Acceptable | 67 | 2.6 |
| EX 2 | 45.5 | 30.0 | 14.6 | 5.7 | | 4.2 | | | 70 | 60 | 72 | 580 | Acceptable | 41 | 2.6 |
| EX 3 | 43.6 | 28.9 | 14.0 | 5.5 | | | 8.0 | | 70 | 60 | 65 | 300 | Acceptable | 31 | 2.5 |
| EX 4 | 38.8 | 27.7 | 17.2 | 5.3 | | | 7.8 | W: 3.2 | 70 | 72 | 78 | 520 | Acceptable | 36 | 2.6 |
| EX 5 | 40.2 | 28.8 | 17.6 | 5.4 | | | 8.0 | B: 0.006 | 70 | 90 | 67 | 765 | Good | 30 | 2.5 |

TABLE 1-continued

| Ex. No | Fe | Ni | Co | Al | Ti | Nb | Ta | Other elements | Cold working ratio after final annealing (%) | Aging treatment time (h) | Young's modulus (Ga) | 0.2% Yield strength (MPa) | Superelastic strain | Difference between Af point and Ms point (° C.) | Abundance of <100> in rolling direction |
|---|---|---|---|---|---|---|---|---|---|---|---|---|---|---|---|
| EX 6 | 40.2 | 28.8 | 17.6 | 5.4 | | | 8.0 | B: 0.01 | 50 | 90 | 52 | 788 | Acceptable | 32 | 2.3 |
| EX 7 | 40.2 | 28.8 | 17.6 | 5.4 | | | 8.0 | B: 0.01 | 75 | 90 | 51 | 772 | Good | 30 | 2.8 |
| EX 8 | 40.2 | 28.8 | 17.6 | 5.4 | | | 8.0 | B: 0.01 | 90 | 90 | 50 | 760 | Good | 31 | 6.4 |
| EX 9 | 40.2 | 28.8 | 17.6 | 5.4 | | | 8.0 | B: 0.01 | 98 | 90 | 51 | 748 | Excellent | 32 | 11 |
| CE 1 | 49.5 | 34.0 | 10.0 | 6.5 | | | | | 70 | 13 | 31 | 400 | No Good | 200 | 2.6 |
| CE 2 | | 50.0 | | | 50.0 | | | | — | — | 31 | 536 | Good | — | — |

The temperature width of the thermal hysteresis of martensitic transformation and reverse transformation (temperature width=difference between Af point (reverse transformation finish temperature) and the Ms point (martensitic transformation start temperature)), the abundance of the crystal orientation <100> in the rolling direction, the superelastic strain (superelasticity), the Young's modulus, and the 0.2% yield strength for Examples 1 to 9 and Comparative Example 1 were measured by the following methods. The results are shown in Table 1.

(1) Temperature Width of Thermal Hysteresis (Difference Between Af Point and Ms Point)

The Ms point and the Af point for the plate were determined by electric resistance measurement (see FIG. 10), and the difference therebetween was treated as the temperature width of the thermal hysteresis. Measurement results for Examples 1 to 9 and Comparative Example 1 are shown in Table 1.

(2) Abundance of <100> in Rolling Direction

The abundance, in the rolling direction of the plate obtained, of a specific crystal orientation in the γ phase was measured using an electron backscatter diffraction pattern measuring apparatus (manufactured by TexSEM Laboratories, Inc. (TSL) under the trade name Orientation Imaging Microscope). Measurement results for Examples 1 to 9 and Comparative Example 1 are shown in Table 1.

The abundance of the crystal orientation was determined by using analysis software (Orientation Imaging Microscope Software Version 3.0 available from TSL) following measurement of the crystal orientation by the electron backscatter diffraction (EBSD) pattern method using the electron backscatter diffraction pattern measuring apparatus. More specifically, the abundance was calculated by an analytical process using a harmonic function incorporated in the analysis software with the expansion order being 16 and the half-width when applied to a Gaussian distribution being 5 degrees. The case where the crystal orientation was not aligned at all with the working direction was regarded as "0", the case where the crystal orientation was random as "1" and the case where a larger abundance value of <100> in the working direction indicates, the crystal orientation is more aligned in a specific direction.

(3) Superelastic Strain (Superelasticity)

Figure 12:
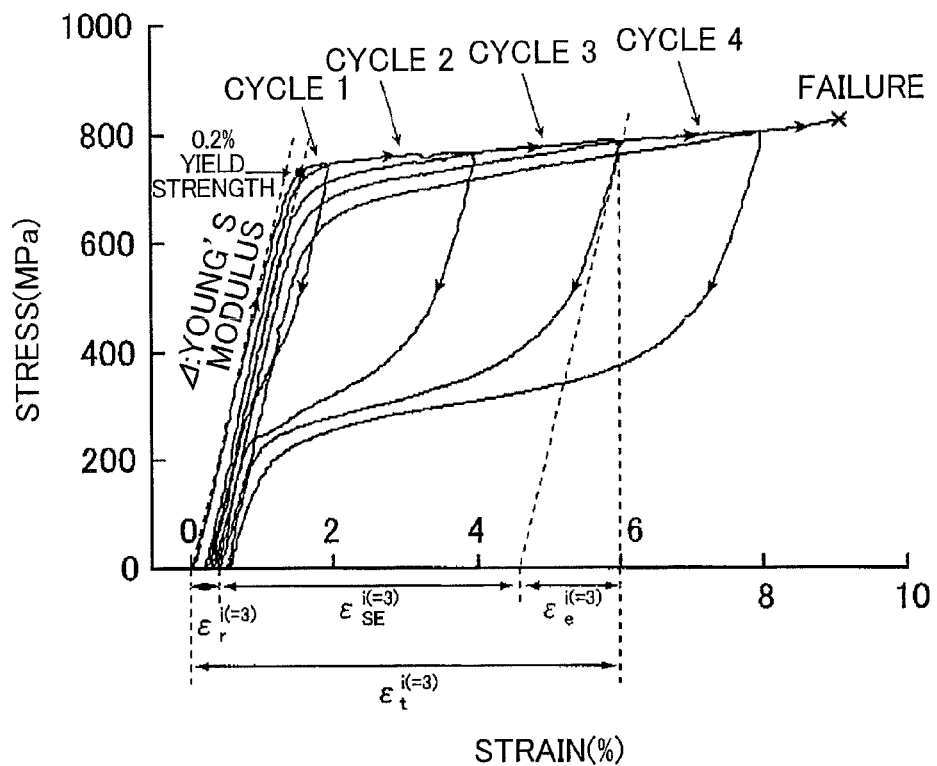
FIG. 12 is a stress-strain curve which is obtained in a tension cycling test on a plate at room temperature, and from which the superelastic strain, Young's modulus and strength (0.2% yield strength) can be determined.

The superelastic strain was determined from stress-strain curves obtained by a tension cycling test on the plate at room temperature. Typical measurement results are shown in FIG. 12. In the tension cycling test, a single cycle consisted of applying a fixed strain to the initial specimen length and subsequently removing the load. The applied strain started at 2% in Cycle 1 and was increased by 2% in each successive cycle (to 4% in Cycle 2, and 6% in Cycle 3), the process being repeated until the specimen failed. The superelastic strain ($\epsilon_{SE}^i$) for the $i^{th}$ cycle was determined, as shown in FIG. 12, by the following formula from the stress-strain curve obtained for that particular cycle.

$$\epsilon_{SE}^i(\%) = \epsilon_t^i - \epsilon_r^i - \epsilon_e^i$$

In the formula, i is the cycle number, $\epsilon_t^i$ is the strain applied in the $i^{th}$ cycle, $\epsilon_r^i$ is the residual strain in the $i^{th}$ cycle, and $\epsilon_e^i$ is the pure elastic deformation strain in the $i^{th}$ cycle.

Figure 13:
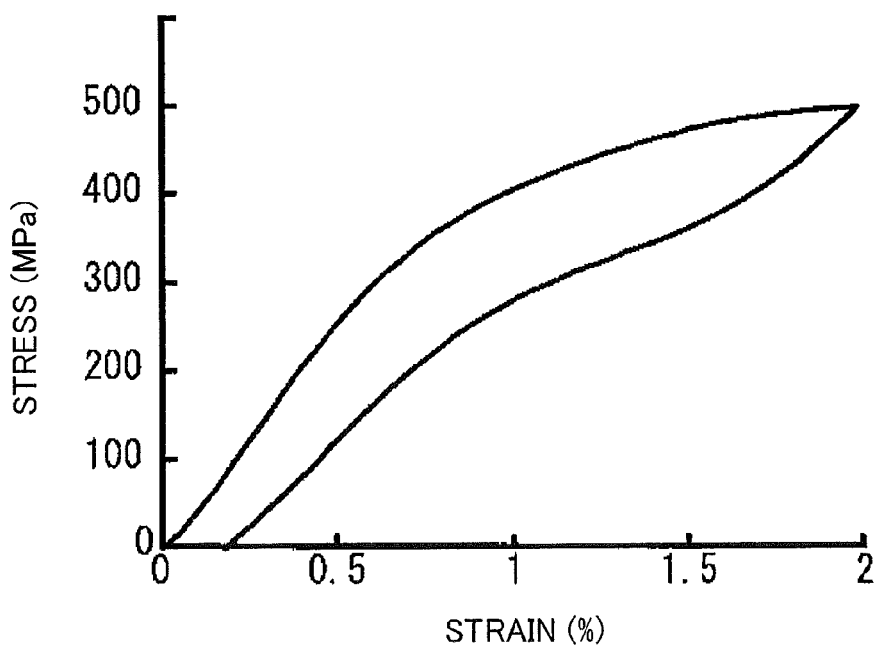
FIG. 13 is a stress-strain correlation diagram at an applied strain of 2% for the ferrous alloy plate of Example 3.

The maximum superelastic strain achievable up until failure of the plate was rated according to the following criteria. FIG. 13 shows the stress-strain curve when the maximum strain on the plate in Example 3 was 2%.

Maximum superelastic strain was 8% or more:
  Excellent
Maximum superelastic strain was at least 2% but less than 8%:
  Good
Maximum superelastic strain was at least 0.5% but less than 2%:
  Acceptable
Maximum superelastic strain was less than 0.5%:
  No Good Measurement results obtained for Examples 1 to 9 and Comparative Example 1 are shown in Table 1.

(4) Young's Modulus and 0.2% Yield Strength

As shown in FIG. 12, the Young's modulus and the 0.2% yield strength were measured from the stress-strain correlation diagram obtained in tension tests at room temperature. Measurement results obtained for Examples 1 to 9 and Comparative Example 1 are shown in Table 1.

As is apparent from Table 1, each of Examples 1 to 9, wherein the temperature width of the thermal hysteresis between the martensitic transformation and the reverse transformation was up to 100° C., exhibited a superelasticity having a maximum superelastic strain of at least 0.5%. However, in Comparative Example 1, wherein the thermal hysteresis temperature width was 200° C., the superelasticity was less than 0.5%. These results show that the ferrous alloys in Examples 1 to 9 for which the temperature width of the thermal hysteresis was small have a better superelasticity than the ferrous alloy in Comparative Example 1 for which the temperature width of the thermal hysteresis was large.

Figure 14A:
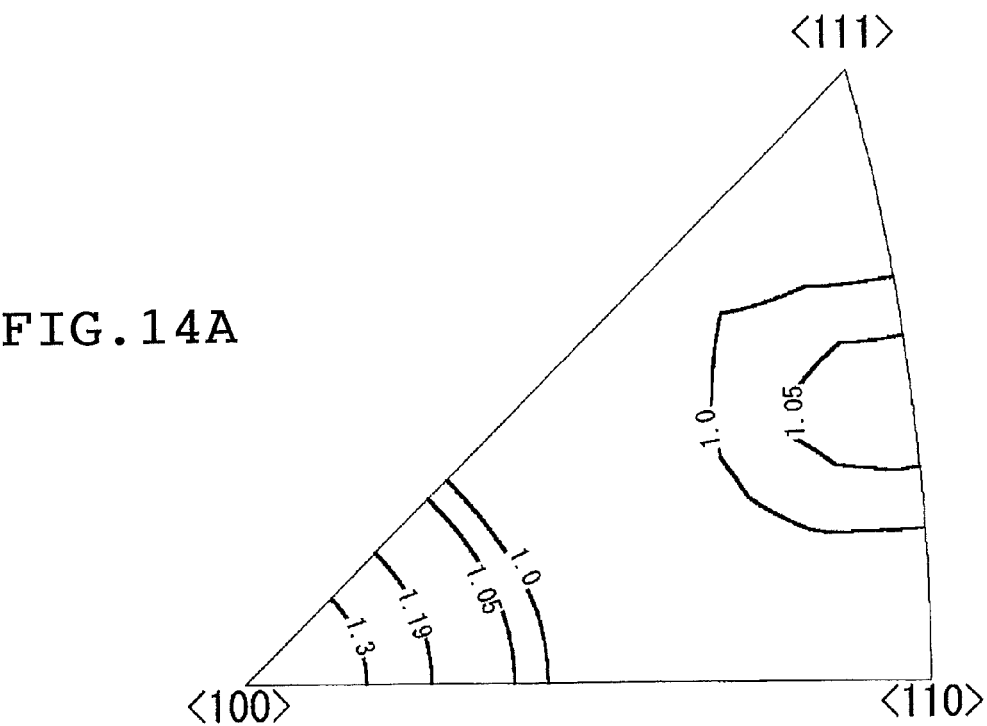
FIGS. 14A and 14B show inverse pole figures which indicate as contour lines the abundance of γ phase crystal orientations in the rolling direction of ferrous alloy plates obtained in Example 6 (FIG. 14A) and Example 9 (FIG. 14B)
Figure 14B:
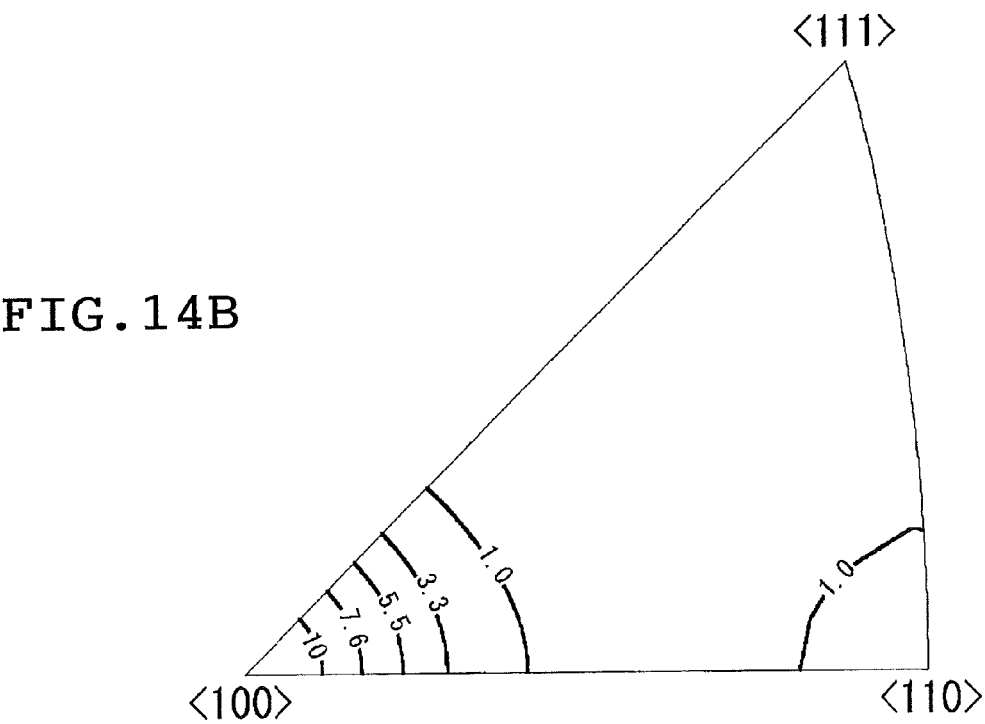

The ferrous alloys in Examples 6 to 9 are alloys of the same composition that were produced under different conditions in the annealing to aging treatment operations. These alloys each have recrystallization textures with differing degrees of alignment for specific crystal orientations in the γ phase. FIGS. 14A and 14B show inverse pole figures which indicate as contour lines the abundance of various crystal orientations in the rolling direction of the plate obtained in Example 6 (FIG. 14A) and the plate obtained in Example 9 (FIG. 14B). In FIG. 14A of the plate obtained in Example 6, the contour lines are clustered in the <100> direction, indicating that the <100> direction is aligned with the rolling direction. The abundance ratio of <100> in the rolling direction was 2.3. In FIG. 14B of the plate obtained in Example 9, the abundance ratio of <100> in the rolling direction was 11.0, indicating that the <100> orientation was even more strongly aligned with the rolling direction. Hence, in the ferrous alloys of the invention, the larger the total cold working ratio after final annealing, the more strongly the specific crystal orientations of the γ phase are aligned with the rolling direction.

Figure 15:
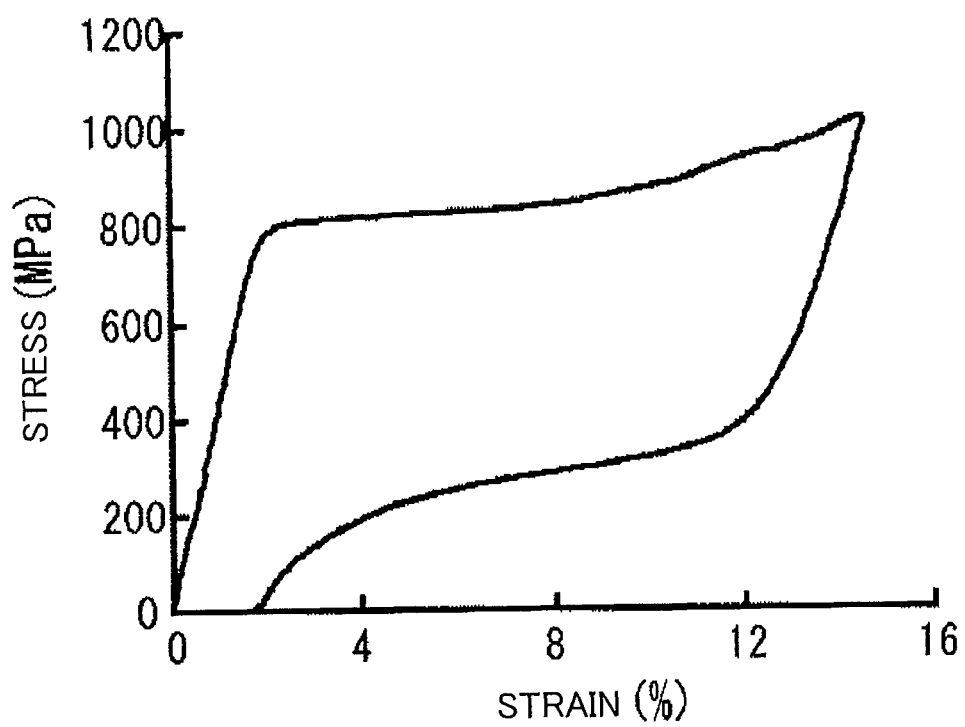
FIG. 15 is a stress-strain correlation diagram at an applied strain of 15% for the ferrous alloy plate of Example 9.

FIG. 15 is the stress-strain curve when the maximum strain in Example 9 is 15%. It is evident here that a superelastic strain of about 10% can be obtained.

As is apparent from Table 1, ferrous alloys in which the total cold working ratio after final annealing is higher and the specific crystal orientations are more strongly aligned have a larger superelastic strain.

Table 1 also shows the superelasticity, Young's modulus and yield strength of a Ti—Ni alloy as Comparative Example 2. It is apparent that the inventive ferrous alloys which have a small thermal hysteresis and in which specific crystal orientations are strongly aligned are endowed with a larger superelastic strain and a higher Young's modulus and strength than the Ti—Ni alloy.

Guide wires and stents including at least a member made of the ferrous alloy of the invention have been described above, although the inventive ferrous alloys may also be used as a chief or partial material in other medical devices used by being inserted or implanted into the body and other medical devices used outside the body. Examples of such other medical devices include vascular filters, orthodontic wire, artificial tooth roots, catheters, bone plates, intramedullary pins, staples, cerebral artery clips, vasooclusive devices and medical forceps.

Figure 16:
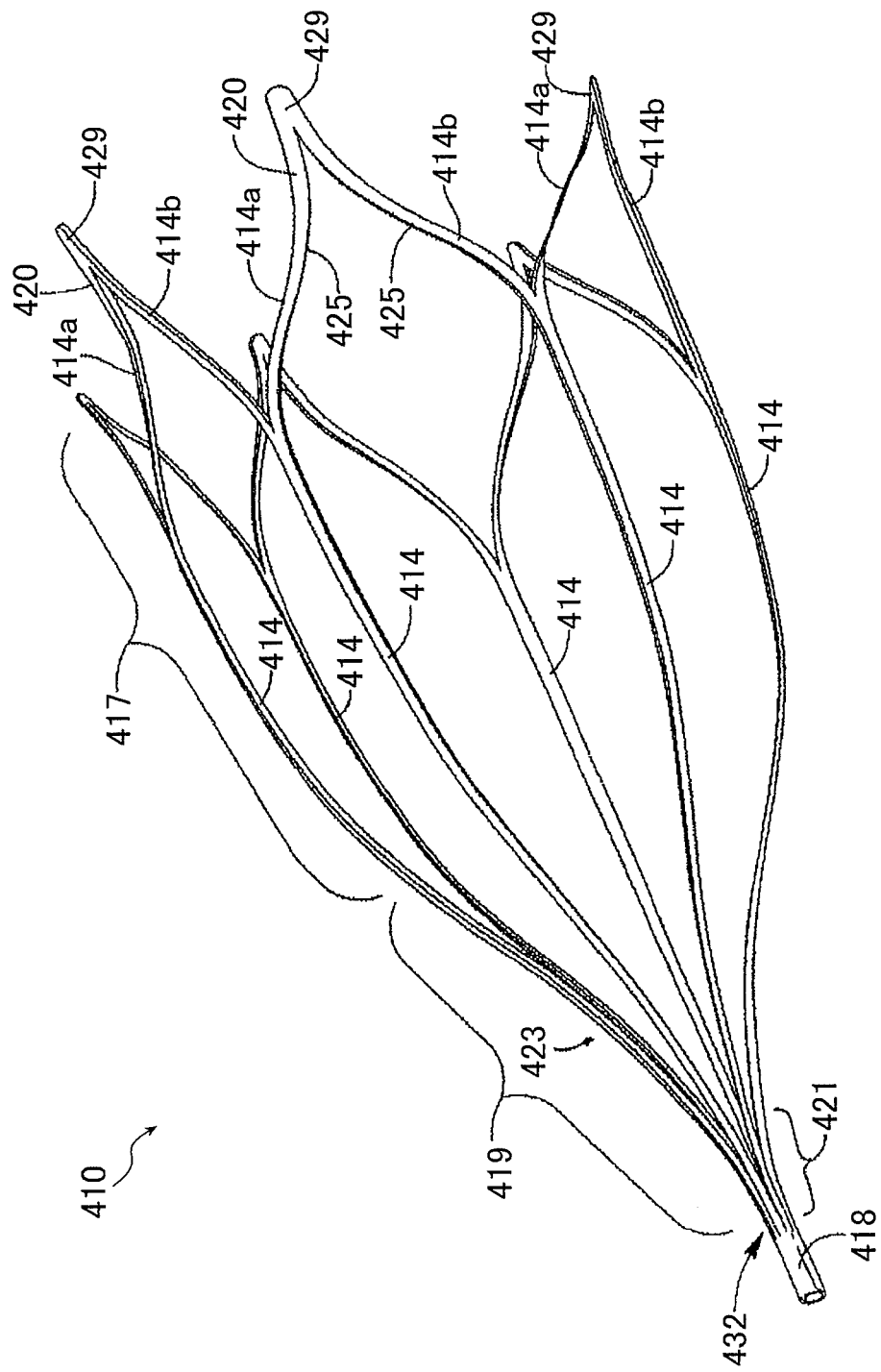
FIG. 16 is a perspective view of a vascular filter composed of the ferrous alloy of the invention.

FIG. 16 is a perspective view of a vascular filter composed of the ferrous alloy of the invention. The vascular filter 410 shown in FIG. 16 is a device which is designed so as to be intravascularly advanced to the inferior vena cava, for example, where it is expanded and functions to prevent thrombus migration from the lower part of the body to the heart and lungs. It generally has a bell-like shape. The vascular filter 410 has an outwardly flaring region 417 and has a convergent zone 421 in a filtration region 419. The filter 410 has a size in the transverse direction at the flaring (or attachment/securing) region 417 which is larger than that at the filtration region 419. In the outwardly flaring region 417, elongated struts 414 having open intervals as shown in FIG. 16 extend out at some fixed angle from the longitudinal axis of the vascular filter 410. In the filtration region 419 which begins at an intermediate portion (the place of transition between the outwardly flaring region 417 and the filtration region 419) of the filter, the struts 414 curve or bend inward (region 423) toward the longitudinal axis, then extend inward at some fixed angle with respect to a tubular portion 418, thereby forming some fixed angle with the longitudinal axis.

At the flaring or attachment (securing) region 417, each strut 414 divides into two joined strut portions 414a and 414b. Strut portions 414a and 414b of each divided strut 414 include curved regions 425 which extend in opposite directions toward corresponding strut portions 414a and 414b of the respectively neighboring struts. The joined strut portion 414a on one strut and a separate strut portion 414b converge at an end 429 of the filter to form a substantially V-shaped region.

The vascular filter composed of the ferrous alloy of the invention may serve as an element of a thrombus capturing device which has a shaft to enable insertion into and removal from a vascular lumen, and which can operate the filter between an expanded state and a contracted state.

The blood filter made of the ferrous alloy of the invention has excellent fluoroscopic visualization properties, making it easy to determine the placement position. Moreover, it is adaptable to various vascular diameters and, in the contracted state, is capable of achieving a very narrow outer diameter, making it easy to insert into a desired blood vessel.

Figure 17:
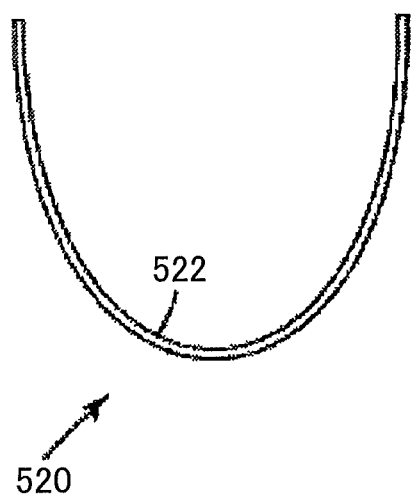
FIG. 17 is a perspective view of an orthodontic wire composed of the ferrous alloy of the invention.

FIG. 17 is a perspective view of an orthodontic wire composed of the ferrous alloy of the invention. The orthodontic wire 520 shown in FIG. 17 has a curved portion 522 which is substantially U-shaped in a top view. The orthodontic wire 520 has a cross-sectional shape that is substantially square, but may instead be round. Because the Young's modulus and 0.2% yield strength are larger than those for conventional Ti—Ni alloys, the same corrective force is achieved with a smaller cross-section, thus making it possible to use smaller brackets and reducing patient discomfort when worn. Moreover, because the orthodontic wire 520 is made of the above-described ferrous alloy and has a larger superelasticity, the number of adjustments made to the wire can be reduced.

What is claimed is:

1. A stent comprising:
   a stent body;
   wherein said stent body is formed from a ferrous alloy which has shape memory properties and superelasticity, said ferrous alloy including a substantially dual phase structure defined by a γ phase and a γ' phase having a difference of 100° C. or less between a reverse transformation finish temperature and a martensitic transformation start temperature in a thermal hysteresis of martensitic transformation and reverse transformation, the ferrous alloy including from 30 to 50% by mass of iron and from 0.001 to 1% by mass of boron;
   wherein said ferrous alloy further includes from 7.8 to 8.0% by mass of tantalum; and
   wherein the stent is configured for insertion into a living body.

2. The stent of claim 1, wherein the stent body includes a plurality of undulating bends provided in an axial direction.

3. The stent of claim 1, wherein the stent body is composed of braided wire.

4. The stent of claim 1, wherein the stent body has a wall thickness of 0.2 mm or less.

5. The stent of claim 4, wherein the stent body has a wall thickness of 0.10 mm or less.

6. The stent of claim 1, wherein the ferrous alloy includes from 38.8 to 46.4% by mass of iron.

7. The stent of claim 1, wherein an abundance of a specific crystal orientation in a working direction of a worked portion for the ferrous alloy is at least 2.0.

8. The stent of claim 1, wherein the ferrous alloy includes from 0.002 to 0.7% by mass of boron.

9. The stent of claim 1, wherein the ferrous alloy includes from 0.006 to 0.01% by mass of boron.

10. The stent of claim 1, wherein the stent body includes a plurality of undulating rings united by partly shared linear segments configured to exhibit a uniform expansion retaining force, each said undulating ring including a plurality of first-side bends and a plurality of second-side bends, and said plurality of linear segments include a plurality of short linear segments and a plurality of long linear segments.

11. A stent comprising:
    a stent body comprising a ferrous alloy having shape memory properties and superelasticity, said ferrous alloy including a two phase structure defined by a γ phase and a γ' phase having a difference of 100° C. or less between a reverse transformation finish temperature and a martensitic transformation start temperature in a thermal hysteresis of martensitic transformation and reverse transformation;

the ferrous alloy comprising a composition which includes from 25 to 35% by mass of nickel, from 10 to 30% by mass of cobalt, and from 2 to 8% by mass of aluminum, the composition including a total of from 1 to 20% by mass of at least one selected from the group consisting of from 1 to 5% by mass of titanium, from 2 to 10% by mass of niobium, from 3 to 20% by mass of tantalum, and the balance being from 35 to 50% by mass of iron and inadvertent impurities; and wherein the stent being configured for insertion into a living body.

12. The stent of claim 11, wherein an abundance of a specific crystal orientation in a working direction of a worked portion for the ferrous alloy is at least 2.0.

13. The stent of claim 11, wherein the ferrous alloy includes from 38.8 to 46.4% by mass of iron.

14. The stent of claim 11, wherein the stent body includes a plurality of undulating bends provided in an axial direction.

15. The stent of claim 11, wherein the stent body is composed of braided wire.

16. The stent of claim 11, wherein the stent body has a wall thickness of 0.2 mm or less.

17. The stent of claim 16, wherein the stent body has a wall thickness of 0.10 mm or less.

18. The stent of claim 11, wherein the ferrous alloy comprises a composition which includes from 25 to 35% by mass of nickel, from 10 to 30% by mass of cobalt, from 2 to 8% by mass of aluminum, from 3 to 20% by mass of tantalum, and the balance being from 35 to 50% by mass of iron and inadvertent impurities.

19. The stent of claim 11, wherein the stent body includes a plurality of undulating rings united by partly shared linear segments configured to exhibit a uniform expansion retaining force, each said undulating ring including a plurality of first-side bends and a plurality of second-side bends, and said plurality of linear segments include a plurality of short linear segments and a plurality of long linear segments.

* * * * *